US007943803B2

(12) United States Patent
Amanokura et al.

(10) Patent No.: US 7,943,803 B2
(45) Date of Patent: May 17, 2011

(54) CLATHRATE COMPOUND, METHOD FOR CONTROLLING CONCENTRATION OF AQUEOUS AGRICULTURAL CHEMICAL ACTIVE INGREDIENT SOLUTION, AND AGRICULTURAL CHEMICAL FORMULATION

(75) Inventors: Natsuki Amanokura, Ichihara (JP); Tetsuya Sahara, Ichihara (JP); Hiroshi Suzuki, Chiba (JP); Yuichi Maekawa, Fujieda (JP); Kiyoshi Katsuura, Takaoka (JP); Yoshihiro Enomoto, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 12/662,809

(22) Filed: May 4, 2010

(65) Prior Publication Data

US 2010/0274006 A1 Oct. 28, 2010

Related U.S. Application Data

(62) Division of application No. 11/571,975, filed as application No. PCT/JP2005/012837 on Jul. 12, 2005, now Pat. No. 7,737,309.

(30) Foreign Application Priority Data

Jul. 13, 2004 (JP) ................. 2004-205905
Sep. 10, 2004 (JP) ................. 2004-264479

(51) Int. Cl.
*C07C 39/15* (2006.01)
*C07C 49/784* (2006.01)
*C07D 307/02* (2006.01)
*C07D 277/28* (2006.01)
*C07D 417/06* (2006.01)
*C07D 401/06* (2006.01)
*C07D 213/57* (2006.01)
*C07D 213/26* (2006.01)
*C07D 273/04* (2006.01)

(52) U.S. Cl. ........ 568/720; 568/333; 549/495; 548/205; 546/270.7; 546/274.7; 546/330; 546/332; 544/67

(58) Field of Classification Search .................. None
See application file for complete search history.

(56) References Cited

U.S. PATENT DOCUMENTS

| 4,325,201 A | 4/1982 | Lewis et al. |
| 4,672,112 A | 6/1987 | Matolcsy et al. |
| 5,079,000 A | 1/1992 | Takahashi et al. |
| 5,364,977 A | 11/1994 | Asai et al. |
| 5,506,216 A | 4/1996 | Schmidt et al. |
| 6,528,467 B1 | 3/2003 | Takemura et al. |
| 2003/0013612 A1 | 1/2003 | Asrar et al. |

FOREIGN PATENT DOCUMENTS

| EP | 0 621 287 A1 | 10/1994 |
| EP | 0 816 349 A1 | 1/1998 |
| EP | 1 110 454 A2 | 6/2001 |
| GB | 1 453 801 A | 10/1976 |
| JP | 4-316564 A | 11/1992 |
| JP | 5-194711 A | 8/1993 |
| JP | 6-316504 A | 11/1994 |
| JP | A-08-099809 | 4/1996 |
| JP | 8-183704 A | 7/1996 |
| JP | A-11-292723 | 10/1999 |
| JP | 2000-327509 A | 11/2000 |
| JP | 2001-233716 A | 8/2001 |
| JP | A-2004-514682 | 5/2004 |
| WO | WO 86/03939 A1 | 7/1986 |
| WO | WO 02/43494 A2 | 6/2002 |
| WO | WO 2006/111570 A2 | 10/2006 |

OTHER PUBLICATIONS

International Search Report for PCT/JP2005/012837 mailed Oct. 11, 2005.
Patent Abstracts of Japan JP 05-194711 published Aug. 3, 1993.
Database CAPLUS on STN, Acc. No. 1996:391269, Nagai et al., JP 08113502 A (May 7, 1996)(abstract).
Davin et al., "Lignin Primary Structures and Dirigent Sites," Current Opinion in Biotechnology, vol. 16, Issue 4, pp. 407-415, Aug. 2005.
Kegley et al., PAN Pesticide Database, Pesticide Action Network, North America (San Francisco, CA, 2009), www.pesticideinfo.org.
Suzuki, "Inclusion Complexes of a Novel Host, 1,1,2,2-Tetrakis(4-Hydroxyphenyl)Ethane, with Various Guests", Tetrahedron Letters, vol. 33, No. 42, pp. 6319-6322m 1992.
Jan. 4, 2011 Supplementary European Search Report issued in European Application No. 05765708.2.
Dec. 14, 2010 Notice of Reasons for Rejection issued in Japanese Application No. 2006-529058 with English translation.

*Primary Examiner* — Brian J Davis
(74) *Attorney, Agent, or Firm* — Oliff & Berridge, PLC

(57) ABSTRACT

A clathrate compound containing a polymolecular host compound as a host compound and an agricultural chemical active ingredient having a saturated solubility in water at 25° C. of not less than 500 ppm as a guest compound.

6 Claims, 13 Drawing Sheets

CLATHRATE COMPOUND, METHOD FOR CONTROLLING CONCENTRATION OF AQUEOUS AGRICULTURAL CHEMICAL ACTIVE INGREDIENT SOLUTION, AND AGRICULTURAL CHEMICAL FORMULATION

CROSS-REFERENCE TO PRIOR APPLICATION

This is a divisional of application Ser. No. 11/571,975 filed Jan. 11, 2007, which is a National Stage Application of PCT/JP2005/012837 filed Jul. 12, 2005, and claims the benefit of Japanese Patent Application Nos. 2004-205905 filed Jul. 13, 2004 and 2004-264479 filed Sep. 10, 2004. The entire disclosure of the prior applications are hereby incorporated by reference herein in its entirety.

TECHNICAL FIELD

The present invention relates to a clathrate compound containing a polymolecular host compound as a host compound and an agricultural chemical active ingredient having ready water-solubility as a guest compound, a method for controlling the concentration of an aqueous agricultural chemical active ingredient solution, and an agricultural chemical formulation containing the clathrate compound.

BACKGROUND ART

An agricultural chemical active ingredient has generally been used as an agricultural chemical formulation after being formulated. Examples of the agricultural chemical formulation include powders, granules, wettable powders, wettable granules, water-soluble agents, water-soluble liquid formulations, emulsifiable concentrates, and sol formulations.

The agricultural chemical active ingredient having ready water-solubility, for example, acetamiprid, is usually used for water-soluble chemicals, granules, and wettable powders.

Recently, formulations as well as application methods thereof have been developed so as to enhance the safety to humans and environments and to promote laborsaving. For example, formulations have been required which can be stably stored for a long period and do not lose their agricultural chemical potency for a long period even in soil, and which can also exhibit agricultural chemical potency for a long period by controlled release of the agricultural chemical active ingredients.

In contrast, in connection with the present invention, some clathrate compounds containing a tetrakisphenolethane compound as a host compound and a pharmacologic agent as a guest compound are known. For example, Patent Literature 1 describes an epoxy adhesive in which a guest compound such as a curing agent for epoxy resin is included by a polymolecular host compound, and Patent Literature 2 describes a bleaching powder-free slime control agent in which an antibacterial agent such as 5-chloro-2-methyl-4-isothiazolin-3-one is included by a polymolecular host compound such as tetrakisphenols.

[Patent Literature 1] Japanese Unexamined Patent Application, First Publication No. Hei 5-194711
[Patent Literature 2] Japanese Unexamined Patent Application, First Publication No. 2000-327509

DISCLOSURE OF THE INVENTION

Problems to be Solved by the Invention

An object of the present invention is to provide a clathrate compound containing a polymolecular host compound as a host compound and an agricultural chemical active ingredient having ready water-solubility as a guest compound, a method for controlling the concentration of an aqueous agricultural chemical active ingredient solution, and an agricultural chemical formulation which is excellent in sustained releasability, storage stability and stability in soil.

Means for Solving the Problems

The present inventors have prepared and evaluated a clathrate compound containing a polymolecular host compound as a host compound and an agricultural chemical active ingredient having ready water-solubility, for example, acetamiprid, as a guest compound, and succeeded in the preparation of the objective clathrate compound. They have found that the use of the resulting clathrate compound makes it possible to maintain saturated solubility of the agricultural chemical active ingredient in water within a predetermined concentration range, and to obtain sol-like agricultural chemical formulation (sol formulation) which is excellent in sustained releasability, storage stability and stability in soil. Thus, the present invention has been completed.

According to a first aspect of the present invention, a clathrate compound characterized by containing a polymolecular host compound as a host compound, and an agricultural chemical active ingredient having saturated solubility in water at 25° C. of not less than 500 ppm as a guest compound are provided.

In the clathrate compound of the present invention, the polymolecular host compound is preferably a compound having two or more hydroxyl groups and two or more aromatic groups in the molecule thereof and is more preferably either of a tetrakisphenol compound represented by formula (I):

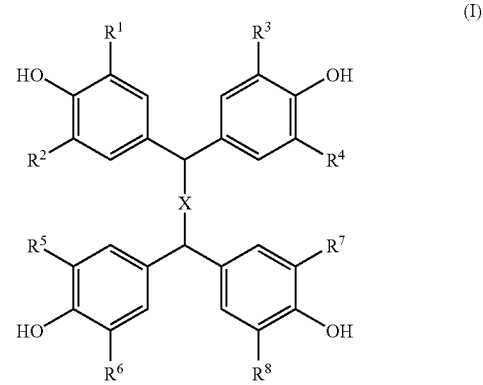

(wherein X represents $(CH_2)_n$ (n represents an integer of 0 to 3) or a phenylene group which may have a substituent, and $R^1$ to $R^8$ each independently represents a hydrogen atom, an alkyl group having 1 to 6 carbon atoms, a phenyl group which may have a substituent, a halogen atom or an alkoxyl group having 1 to 6 carbon atoms), or a hydroxybenzophenone compound represented by formula (II):

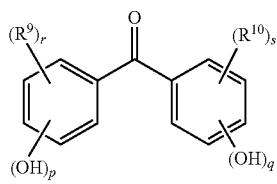

(II)

(wherein $R^9$ and $R^{10}$ each independently represents an alkyl group having 1 to 6 carbon atoms, a halogen atom or an alkoxyl group having 1 to 6 carbon atoms, r and s each independently represents an integer of 0 to 4, and p and q each independently represents an integer of 1 to 4).

In the clathrate compound of the present invention, the agricultural chemical active ingredient is preferably a neonicotinoid compound and the neonicotinoid compound is more preferably at least one selected from the group consisting of nitenpyram, imidacloprid, acetamiprid, thiamethoxam, clotianidin, thiacloprid and dinotefuran.

According to a second aspect of the present invention, a method for controlling the concentration of an aqueous agricultural chemical active ingredient solution is provided, characterized by containing a step of maintaining a saturated solubility of the agricultural chemical active ingredient in water within a predetermined concentration range by including the agricultural chemical active ingredient having saturated solubility in water at 25° C. of not less than 500 ppm in an interior space formed of a polymolecular host compound.

In the concentration control method of the present invention, it is preferable that the saturated solubility of the agricultural chemical active ingredient in water be maintained within a predetermined concentration range by suitably selecting the polymolecular host compound and including the agricultural chemical active ingredient in an interior space formed of the polymolecular host compound.

In the concentration control method of the present invention, the polymolecular host compound is preferably a compound having two or more hydroxyl groups and two or more aromatic groups in the molecule thereof, and more preferably is either of the tetrakisphenol compound represented by formula (I) or the hydroxybenzophenone compound represented by formula (II).

In the concentration control method of the present invention, the agricultural chemical active ingredient is preferably a neonicotinoid compound and the neonicotinoid compound is more preferably at least one selected from the group consisting of nitenpyram, imidacloprid, acetamiprid, thiamethoxam, clotianidin, thiacloprid and dinotefuran.

According to a third aspect of the present invention, an agricultural chemical formulation is provided, characterized by containing the clathrate compound of the present invention.

The agricultural chemical formulation of the present invention is preferably a seed treatment agent.

The agricultural chemical formulation of the present invention is preferably a sol formulation.

According to a fourth aspect of the present invention, an agricultural active composition is provided, characterized by containing the clathrate compound of the present invention and a synthetic pyrethroid.

An agricultural chemical formulation is also provided, characterized by containing the agricultural active composition of the present invention. The agricultural chemical formulation is preferably a seed treatment agent and the agricultural chemical formulation is preferably a sol formulation.

Effects of the Invention

According to the clathrate compound of the present invention, an agricultural chemical formulation can be prepared which can maintain saturated solubility of an agricultural chemical active ingredient having ready water-solubility within a predetermined concentration range and is also excellent in sustained releasability, storage stability and stability in soil.

According to the concentration control method of the present invention, it is made possible to maintain saturated solubility of an agricultural chemical active ingredient having ready water-solubility within a predetermined concentration range. Consequently, elution of the agricultural chemical active ingredient into moisture in the soil can be controlled and thus the persistence of potency thereof is not lowered by environmental change such as rainfall or the like.

The agricultural chemical formulation of the present invention is excellent in sustained releasability, storage stability and stability in soil and can efficiently exhibit active efficacy, and is also environmentally friendly.

The agricultural active composition of the present invention can exhibit active efficacy more efficiently.

In the agricultural chemical formulation containing the clathrate compound of the present invention as a sol formulation, neither particle growth nor caking may substantially occur.

BEST MODE FOR CARRYING OUT THE INVENTION

Figure 1:
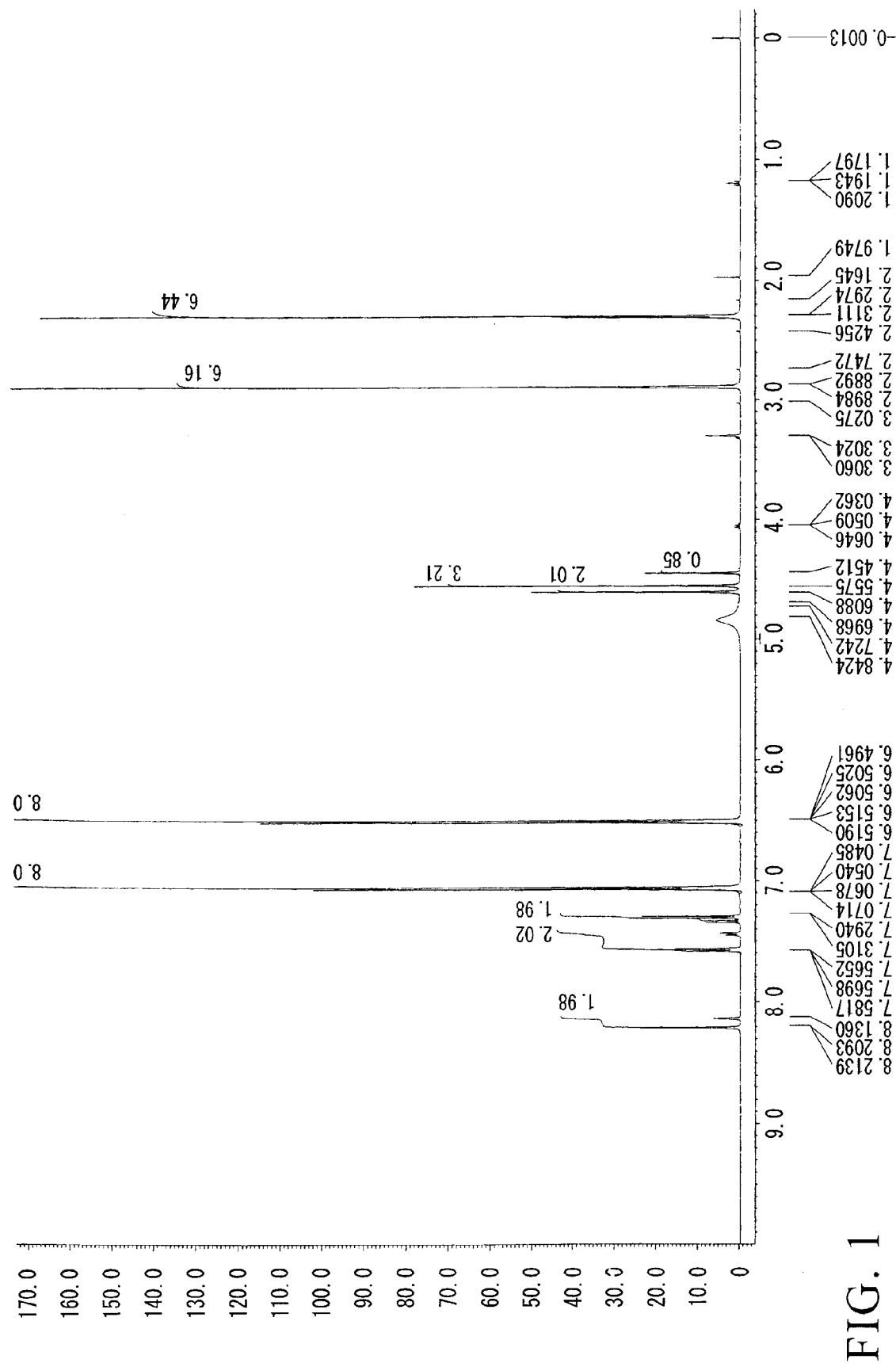
FIG. 1 is a graph showing a $^1$H-NMR spectrum of Clathrate compound 1.

The present invention will now be described in detail with respect to the following items: 1) a clathrate compound, 2) a method for controlling the concentration of an aqueous agricultural chemical active ingredient solution, 3) an agricultural chemical formulation, and 4) an agricultural active composition.

1) Clathrate Compound

The clathrate compound of the present invention is characterized by containing a polymolecular host compound as a host compound and an agricultural chemical active ingredient having saturated solubility in water at 25° C. of not less than 500 ppm as a guest compound.

The polymolecular host compound used in the present invention is a compound in which plural molecules are combined via a hydrogen bond to form a crystal with an interior space and in which a guest compound can be included in the space.

The polymolecular host compound used in the present invention is not specifically limited as long as it is a compound having such a property.

Examples of the polymolecular host compound include compounds having one aromatic group and one hydroxyl group in a molecule thereof, such as phenol, o-chlorophenol, 2,4,6-trichlorophenol, p-chlorophenol, o-nitrophenol, p-nitrophenol, 2,4-dinitrophenol, 2,6-dinitrophenol, 2,4,6-trinitrophenol, p-t-butylphenol, and p-t-octylphenol;

compounds having one aromatic group and two hydroxyl groups in a molecule thereof, such as t-butylhydroquinone and 2,5-di-t-butylhydroquinone;

compounds having two or more aromatic groups and two or more hydroxyl groups in a molecule thereof, such as α,α,α',α'-tetraphenyl-1,1'-biphenyl-2,2'-dimethanol, 4,4'-cyclohexilidenebisphenol, 4,4'-methylenebisphenol, 4,4'-ethylidenebisphenol, 5,5'-methylenedisalicylic acid, bis(4-hydroxyphenyl)sulfide, 4,4'-butylidenebis(3-methyl-6-t-butylphenol), 2,2'-methylenebis(4-methyl-6-t-butylphenol), 4,4'-(1-phenylethylidene)bisphenol, 2,5-bis(2,4-dimethylphenyl)hydroquinone, 1,1,6,6-tetraphenyl-2,4-hexadiyne-1,6-diol, 1,1,4,4-tetraphenyl-2-butyne-1,4-diol, 1,1,2,2-tetraphenylethane-1,2-diol, 1,1,6,6-tetrakis(2,4-dimethylphenyl)-2,4-hexadiyne-1,6-diol, 9,9'-bianthracene, 9,10-bis(4-methylphenyl)-9,10-dihydroanthracene-9,10-diol, 9,10-diphenyl-9,10-dihydroanthracene-9,10-diol, 1,1-bis-2-naphthol, the tetrakisphenol compounds represented by formula (I), and the hydroxybenzophenone compounds represented by formula (II); and other polymolecular host compounds such as 1,4-diazabicyclo-[2.2.2]-octane, granular cornstarch (Porous Y-20), 5,5-dimethylhydantoin, N-phenylmaleimide, and 9,9'-bianthracene.

These polymolecular host compounds can be used alone or in combination of at least two kinds thereof.

Among these, a compound having two or more aromatic groups and two or more hydroxyl groups in a molecule thereof is preferable and a tetrakisphenol compound represented by formula (I) or a hydroxybenzophenone compound represented by formula (II) is more preferable because a clathrate compound containing an agricultural chemical active ingredient having saturated solubility in water at 25° C. of not less than 500 ppm as a guest compound can be obtained efficiently and also an agricultural chemical formulation having excellent sustained releasability, storage stability and stability in soil can be obtained.

In formula (I), X represents $(CH_2)_n$ or a phenylene group which may have a substituent.

n represents an integer of 0 to 3 and is preferably 0.

The phenylene group may be a p-phenylene group, an m-phenylene group or an o-phenylene group, but is preferably a p-phenylene group.

Examples of the substituent of the phenylene group which may have a substituent include halogen atoms such as fluorine, chlorine, and bromine; alkyl groups such as a methyl group, ethyl group, and n-propyl group; and alkoxy groups such as a methoxy group, ethoxy group, and n-propoxy group. Among these, a phenylene group having no substituent is preferable.

$R^1$ to $R^8$ each independently represents a hydrogen atom; an alkyl group having 1 to 6 carbon atoms such as a methyl group, ethyl group, n-propyl group, or isopropyl group; a phenyl group which may have a substituent, such as a phenyl group, 2-chlorophenyl group, 4-methylphenyl group, 2,4-difluorophenyl group, 3,5-dimethoxyphenyl group, or 2,4,6-trimethylphenyl group; a halogen atom such as fluorine, chlorine, or bromine; or an alkoxyl group having 1 to 6 carbon atoms, such as a methoxy group, ethoxy group, n-propoxy group, isopropoxy group, n-butoxy group, or t-butoxy group.

Specific examples of the compound represented by formula (I) include 1,1,2,2-tetrakis(4-hydroxyphenyl)ethane (TEP), 1,1,2,2-tetrakis(3-methyl-4-hydroxyphenyl)ethane, 1,1,2,2-tetrakis(3,5-dimethyl-4-hydroxyphenyl)ethane, 1,1,2,2-tetrakis(3-chloro-4-hydroxyphenyl)ethane, 1,1,2,2-tetrakis(3,5-dichloro-4-hydroxyphenyl)ethane, 1,1,2,2-tetrakis(3-bromo-4-hydroxyphenyl)ethane, 1,1,2,2-tetrakis(3,5-dibromo-4-hydroxyphenyl)ethane, 1,1,2,2-tetrakis(3-t-butyl-4-hydroxyphenyl)ethane, 1,1,2,2-tetrakis(3,5-di-t-butyl-4-hydroxyphenyl)ethane, 1,1,2,2-tetrakis(3-fluoro-4-hydroxyphenyl)ethane, 1,1,2,2-tetrakis(3,5-difluoro-4-hydroxyphenyl)ethane, 1,1,2,2-tetrakis(3-methoxy-4-hydroxyphenyl)ethane, 1,1,2,2-tetrakis(3,5-dimethoxy-4-hydroxyphenyl)ethane, 1,1,2,2-tetrakis(3-chloro-5-methyl-4-hydroxyphenyl)ethane, 1,1,2,2-tetrakis(3-bromo-5-methyl-4-hydroxyphenyl)ethane, 1,1,2,2-tetrakis(3-methoxy-5-methyl-4-hydroxyphenyl)ethane, 1,1,2,2-tetrakis(3-t-butyl-5-methyl-4-hydroxyphenyl)ethane, 1,1,2,2-tetrakis(3-chloro-5-bromo-4-hydroxyphenyl)ethane, 1,1,2,2-tetrakis(3-chloro-5-phenyl-4-hydroxyphenyl)ethane, 1,1,2,2-tetrakis[(4-hydroxy-3-phenyl)phenyl]ethane, 1,1,3,3-tetrakis(4-hydroxyphenyl)propane, 1,1,3,3-tetrakis(3-methyl-4-hydroxyphenyl)propane, 1,1,3,3-tetrakis(3,5-dimethyl-4-hydroxyphenyl)propane, 1,1,3,3-tetrakis(3-chloro-4-hydroxyphenyl)propane, 1,1,3,3-tetrakis(3,5-dichloro-4-hydroxyphenyl)propane, 1,1,3,3-tetrakis(3-bromo-4-hydroxyphenyl)propane, 1,1,3,3-tetrakis(3,5-dibromo-4-hydroxyphenyl)propane, 1,1,3,3-tetrakis(3-phenyl-4-hydroxyphenyl)propane, 1,1,3,3-tetrakis(3,5-diphenyl-4-hydroxyphenyl)propane, 1,1,3,3-tetrakis(3-methoxy-4-hydroxyphenyl)propane, 1,1,3,3-tetrakis(3,5-dimethoxy-4-hydroxyphenyl)propane, 1,1,3,3-tetrakis(3-t-butyl-4-hydroxyphenyl)propane, 1,1,3,3-tetrakis(3,5-di-t-butyl-4-hydroxyphenyl)propane, 1,1,4,4-tetrakis(4-hydroxyphenyl)butane, 1,1,4,4-tetrakis(3-methyl-4-hydroxyphenyl)butane, 1,1,4,4-tetrakis(3,5-dimethyl-4-hydroxyphenyl)butane, 1,1,4,4-tetrakis(3-chloro-4-hydroxyphenyl)butane, 1,1,4,4-tetrakis(3,5-dichloro-4-hydroxyphenyl)butane, 1,1,4,4-tetrakis(3-methoxy-4-hydroxyphenyl)butane, 1,1,4,4-tetrakis(3,5-dimethoxy-4-hydroxyphenyl)butane, 1,1,4,4-tetrakis(3-bromo-4-hydroxyphenyl)butane, 1,1,4,4-tetrakis(3,5-dibromo-4-hydroxyphenyl)butane, 1,1,4,4-tetrakis(3-t-butyl-4-hydroxyphenyl)butane, and 1,1,4,4-tetrakis(3,5-di-t-butyl-4-hydroxyphenyl)butane.

Specific examples thereof further include α,α,α',α'-tetrakis(4-hydroxyphenyl)-p-xylene, α,α,α',α'-tetrakis(4-hydroxyphenyl)-m-xylene, α,α,α',α'-tetrakis(4-hydroxyphenyl)-o-xylene, α,α,α',α'-tetrakis(4-hydroxy-3-methylphenyl)-p-xylene, α,α,α',α'-tetrakis(4-hydroxy-3- chlorophenyl)-p-xylene, α,α,α',α'-tetrakis(4-hydroxy-3-ethylphenyl)-p-xylene, α,α,α',α'-tetrakis(4-hydroxy-3-isopropylphenyl)-p-xylene, α,α,α',α'-tetrakis(4-hydroxy-3-chlorophenyl)-m-xylene, α,α,α',α'-tetrakis(4-hydroxy-3-methylphenyl)-m-xylene, α,α,α',α'-tetrakis(4-hydroxy-3-ethylphenyl)-m-xylene, α,α,α',α'-tetrakis(4-hydroxy-3-methylphenyl)-o-xylene, α,α,α',α'-tetrakis(4-hydroxy-3-chlorophenyl)-o-xylene, α,α,α',α'-tetrakis(4-hydroxy-3-ethylphenyl)-o-xylene, α,α,α',α'-tetrakis(4-hydroxy-3-isopropylphenyl)-o-xylene,
α,α,α',α'-tetrakis(4-hydroxy-3-t-butylphenyl)-p-xylene, α,α,α',α'-tetrakis(4-hydroxy-3-bromophenyl)-p-xylene, α,α,α',α'-tetrakis(4-hydroxy-3-iodophenyl)-p-xylene, α,α,α',α'-tetrakis(4-hydroxy-3-methoxyphenyl)-p-xylene, α,α,α',α'-tetrakis(4-hydroxy-3-ethoxyphenyl)-p-xylene, α,α,α',α'-tetrakis(4-hydroxy-3-isopropoxyphenyl)-p-xylene, α,α,α',α'-tetrakis(4-hydroxy-3-t-butoxyphenyl)-p-xylene, α,α,α',α'-tetrakis(3-hydroxyphenyl)-p-xylene, α,α,α',α'-tetrakis(3-hydroxy-4-chlorophenyl)-p-xylene, α,α,α',α'-tetrakis(3-hydroxy-4-bromophenyl)-p-xylene, α,α,α',α'-tetrakis(3-hydroxy-4-iodophenyl)-p-xylene, α,α,α',α'-tetrakis(3-hydroxy-4-methoxyphenyl)-p-xylene, α,α,α',α'-tetrakis(3-hydroxy-4-ethoxyphenyl)-p-xylene, α,α,α',α'-tetrakis(2-hydroxyphenyl)-p-xylene, α,α,α',α'-tetrakis(2-hydroxy-4-chlorophenyl)-p-xylene, α,α,α',α'-tetrakis(2-hydroxy-4-methylphenyl)-p-xylene, α,α,α',α'-tetrakis(2-hydroxy-4-methoxyphenyl)-p-xylene, α,α,α',α'-tetrakis(4-hydroxy-3,5-dichlorophenyl)-p-xylene, α,α,α',α'-tetrakis(4-hydroxy-3,5-dimethylphenyl)-p-xylene, α,α,α',α'-tetrakis(4-hydroxy-3-chloro-5-methylphenyl)-p-xylene, α,α,α',α'-tetrakis(4-hydroxyphenyl)-3-chloro-p-xylene, α,α,α',α'-tetrakis(4-hydroxyphenyl)-3-methyl-p-xylene, α,α,α',α'-tetrakis(4-hydroxyphenyl)-3-methoxy-p-xylene, α,α-bis(4-hydroxyphenyl)-α',α'-bis(3-chloro-4-hydroxyphenyl)-p-xylene, α,α-bis(4-hydroxyphenyl)-α',α-bis(3-methyl-4-hydroxyphenyl)-p-xylene, α,α-bis(4-hydroxyphenyl)-α',α-bis(3-methoxy-4-hydroxyphenyl)-p-xylene, α,α,α'-tris(4-hydroxyphenyl)-α'-3-chlorophenyl-p-xylene, α,α,α'-tris(4-hydroxyphenyl)-α'-3-methylphenyl-p-xylene, and α,α,α'-tris(4-hydroxyphenyl)-α'-3-methoxyphenyl-p-xylene.

In formula (II), $R^9$ and $R^{10}$ each independently represents an alkyl group having 1 to 6 carbon atoms, a halogen atom or an alkoxyl group having 1 to 6 carbon atoms. The alkyl group having 1 to 6 carbon atoms, the halogen atom and the alkoxyl group having 1 to 6 carbon atoms are the same as those described as the alkyl group having 1 to 6 carbon atoms, the halogen atom and the alkoxyl group having 1 to 6 carbon atoms in formula (I).

r and s each independently represents an integer of 0 to 4 and is preferably 0. p and q each independently represents an integer of 1 to 4 and is preferably 1 or 2.

Specific examples of the compound represented by formula (II) include 4,4'-dihydroxybenzophenone, 2,4'-dihydroxybenzophenone, 3,4'-dihydroxybenzophenone, 3,3'-dihydroxybenzophenone, 2,3'-dihydroxybenzophenone, 2,2'-dihydroxybenzophenone, 4,4'-dihydroxy-2-methylbenzophenone, 4,4'-dihydroxy-3-methylbenzophenone, 4,4'-dihydroxy-2-chlorobenzophenone, 4,4'-dihydroxy-3-chlorobenzophenone, 4,4'-dihydroxy-2-methoxybenzophenone, 4,4'-dihydroxy-3-methoxybenzophenone, 4,4'-dihydroxy-2-dimethylbenzophenone, 4,4'-dihydroxy-3,3'-dimethylbenzophenone, 4,4'-dihydroxy-2,2'-dimethylbenzophenone, 4,4'-dihydroxy-3,3'-dichlorobenzophenone, 4,4'-dihydroxy-2,2'-dimethoxybenzophenone, 4,4'-dihydroxy-2,2'-dimethoxybenzophenone, 3,3'-dihydroxy-2,2'-dimethylbenzophenone, 3,3'-dihydroxy-4,4'-dimethylbenzophenone, 2,2'-dihydroxy-3,3'-dimethylbenzophenone, 2,2'-dihydroxy-4,4'-dimethylbenzophenone, 2,2',4,4'-tetrahydroxybenzophenone, 2,2',3,3'-tetrahydroxybenzophenone, 3,3',4,4'-tetrahydroxybenzophenone, 2,2',3,4'-tetrahydroxybenzophenone, 3,3',2,4'-tetrahydroxybenzophenone, 4,4',3,2'-tetrahydroxybenzophenone, 2,3,4,4'-tetrahydroxybenzophenone, 2,2',4,4'-tetrahydroxy-3,3'-dimethylbenzophenone, 2,2',4,4'-tetrahydroxy-3,3'-dichlorobenzophenone, and 2,2',4,4'-tetrahydroxy-3,3'-dimethoxybenzophenone.

The agricultural chemical active ingredient to be used is not specifically limited as long as it is an agricultural chemical active ingredient having saturated solubility in water at 25° C. of not less than 500 ppm (also referred to as an "agricultural chemical active ingredient having ready water-solubility", hereinafter).

Examples of the agricultural chemical active ingredient having ready water-solubility include neonicotinoid compounds such as (E)-N-(6-chloro-3-pyridylmethyl)-N-ethyl-N'-methyl-2-nitrovinylidenediamine [common name: nitenpyram, aqueous solubility: about 2000 ppm], (E)-N1-[(6-chloro-3-pyridyl)methyl]-N2-cyano-N1-methylacetamidine [common name: acetamiprid, aqueous solubility in water: 4200 ppm (25° C.)], 1-(6-chloro-3-pyridylmethyl)-N-nitroimidazolidin-2-ylideneamine [common name: imidacloprid, aqueous solubility: 510 ppm (20° C.)], 3-(2-chloro-1,3-thiazole-5-methyl-1,3,5-oxadiazinan-4-ylidene [common name: thiamethoxam, aqueous solubility: 4100 ppm (25° C.)], (E)-1-(2-chloro-1,3-thiazol-5-ylmethyl-3-methyl-2-nitroguanidine [common name: clotianidin, aqueous solubility: 0.327 g/L (20° C.)], 3-(6-chloro-3-pyridylmethyl)-1,3-thiazolidin-2-ylidenecyanamide (common name: thiacloprid), and (RS)-1-methyl-2-nitro-3-(tetrahydro-3-furylmethyl)guanidine (common name: dinotefuran);

phosphorus compounds such as O,S-dimethyl-N-acetylphosphoroamide thioate [common name: acephate, about 650000 ppm], N2-(4-chloro-o-toluyl)-N1,N1-dimethylformamide [aqueous solubility: 250 ppm (20° C.)], and 2,2-dichlorovinyldimethyl phosphate [common name: DDVP, aqueous solubility: about 1000 ppm (room temperature)]; carbamate compounds such as 2,2-dimethyl-1,3-benzodioxol-4-yl-methylcarbamate•hydrochloride [common name: bendiocarb, aqueous solubility: 26000 ppm (25° C.)], S,S'-2-dimethylaminotrimethylene-bis(thiocarbamate) [common name: cartap, aqueous solubility: 200000 ppm (25° C.)], and 2-ethylthiomethylphenylmethylcarbamate [common name:ethiofencarb, aqueous solubility: 1800 ppm (20° C.)]; and other insecticidal compounds such as S-methyl-N,N-dimethyl-N-methylcarbamoyloxy-1-thiooxam imidate [common name: oxamyl, aqueous solubility: 280000 ppm], S-methyl-N-(methylcarbamoyloxy)thioacetoimidate [common name: methomyl, aqueous solubility: 58000 ppm], and 1,3-dichloropropene [common name: D-D, aqueous solubility: 2000 ppm].

Among these compounds, the agricultural chemical active ingredient is preferably a neonicotinoid compound and the neonicotinoid compound is more preferably at least one selected from the group consisting of nitenpyram, imidacloprid, acetamiprid, thiamethoxam, clothianidin, thiacloprid and dinotefuran in the present invention.

These agricultural chemical active ingredients can be used alone or in combination of at least two kinds thereof mixed in an arbitrary ratio. Among these, acetamiprid is particularly preferable because it has high agricultural chemical activity and exerts remarkable effects in forming a clathrate compound.

The method for preparing the clathrate compound of the present invention is not specifically limited and a conventionally known method for preparing a clathrate compound using a polymolecular host compound can be employed.

Specific examples of the method include (i) a method of adding a polymolecular host compound to a liquid agricultural chemical active ingredient, followed by stirring, (ii) a method of adding a polymolecular host compound to a solvent solution of a solid agricultural chemical active ingredient, followed by stirring, and (iii) a method of mixing a solid agricultural chemical active ingredient with a powdered polymolecular host compound.

When methods (i) to (iii) are employed, the stirring temperature is usually from room temperature to 100° C., and the stirring time is usually from several minutes to several tens of hours.

The mixing ratio of the polymolecular host compound to the agricultural chemical active ingredient as the guest compound varies depending on the kind of compound to be used, and a ratio of the polymolecular host compound: the agricultural chemical active ingredient is generally from 99:1 to 1:99 (parts by weight), a ratio of the polymolecular host compound: the agricultural chemical active ingredient is preferably from 80:20 to 20:80 (parts by weight), a ratio of the polymolecular host compound: the agricultural chemical active ingredient is more preferably from 60:40 to 35:65 (parts by weight).

Examples of the solvent to be used include water; alcohols such as methanol and ethanol; esters such as ethyl acetate; and halogenated hydrocarbons such as dichloromethane.

The amount of solvent is not specifically limited as long as it enables stirring and mixing with ease as well as after-treatment with ease.

The objective clathrate compound can be isolated according to conventional separation and purification methods from the mixture obtained by stirring.

The structure of the resulting clathrate compound can be checked by well-known analytical methods such as NMR spectrometry, IR spectrometry, and mass spectrometry.

The obtained clathrate compound can be formed into a sol solution having high dispersion stability, as described hereinafter.

The melting point of the obtained clathrate compound is not influenced by the agricultural chemical active ingredient or solvent to be used, but is influenced by the polymolecular host compound to be used. For example, when acetamiprid having a melting point of 96.25° C. is used as the agricultural chemical active ingredient, a clathrate compound having a melting point of about 165° C. is obtained by using 1,1,2,2-tetrakis(4-hydroxyphenyl)ethane (TEP) as the polymolecular host compound, and a clathrate compound having a melting point of about 135° C. is obtained by using 2,2',4,4'-tetrahydroxybenzophenone.

The clathrate compound of the present invention can be mixed with other fungicides or insecticides so as to broaden the biological application range. Specific examples to be mixed include, but are not limited to, the following.

Fungicides:
Copper agents; basic copper chloride, basic copper sulfate, and the like.
Sulfur agents; thiuram, zineb, maneb, mancozeb, ziram, propineb, polycarbamate, and the like.
Polyhaloalkylthio agent; captan, folpet, dichlorofluanide, and the like.
Organic chlorine agents; chlorothalonil, fthalide, and the like.
Organophosphorus agents; IBP, EDDP, tolclofos-methyl, pyrazophos, fosetyl, and the like.
Benzimidazole agents; thiophanate-methyl, benomyl, carbendazim, thiabendazole, and the like.
Dicarboxyimide agents; iprodione, procymidone, vinclozolin, fluoroimide, and the like.
Carboxyamide agents; oxycarboxin, mepronil, flutolanil, tecloftalam, trichlamide, pencycuron, and the like.
Acylalanine agents; metalaxyl, oxadixyl, furalaxyl, and the like.
Methoxyacrylate agents; kresoxim-methyl, azoxystrobin, metominostrobin, and the like.
Anilinopyrimidine agents; andpurine, mepanipyrim, pyrimethanil, cyprodinil, and the like.
SBI agents; triadimefon, triadimenol, bitertanol, myclobutanil, hexaconazole, propiconazole, triflumizole, prochloraz, pefurazoate, fenarimol, pyrifenox, triforine, flusilazole, etaconazole, diclobutrazol, fluotrimazole, flutriafen, penconazole, diniconazole, imazalil, tridemorph, fenpropimorph, buthiobate, epoxiconazole, metoconazole, and the like.
Antibiotics; polyoxin, blasticiden S, kasugamycin, validamycin, dihydrostreptomycin sulfate, and the like. Others; propamocarb hydrochloride, quintozene, hydroxyisoxazole, methasulfocarb, anirazine, isoprothiolane, probenazole, chiomethionat, dithianon, dinocap, diclomezine, ferimzone, fluazinam, pyroquilon, tricyclazole, oxolinic acid, dithianon, iminoctadine acetate, cymoxanil, pyrrolnitrin, methasulfocarb, diethofencarb, binapacryl, lecithin, sodium bicarbonate, fenaminosulf, dodine, dimethomorph, phenazine oxide, carpropamid, flusulfamide, fludioxonil, famoxadone, and the like.
Insecticides/Acarcides:
Organophosphorus and carbamate insecticides; fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydimeton-methyl, ethion, salithion, cyanophos, isoxathion, pyridaphenthion, phosalone, methidathion, sulprofos, chlorfenvinphos, tetrachlorvinphos, dimethylvinphos, propaphos, isophenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, phenoxycarb, and the like. Pyrethroid insecticides; permethrin, cypermethrin, deltamethrin, fenvalerate, fenpropathrin, pytethrin, allethrin, tetramethrin, resmethrin, dimethrin, propathrin, phenothrin, protryne, fluvalinate, cyfluthrin, cyhalothrin, fucythrinate, ethofenprox, cycloprotryne, tralomethrin, silafluofen, brofenprox, acrinathrin, and the like. Benzoylurea and other insecticides; diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulphate, rotenone, metaldehyde, machine oil, microorganism pesticides such as BT and insect pathogenic virues; pheromone agents, and the like.

Nematicides; fenamiphos and fosthiazate

Acaricides; chlorobenzilate, phenisobromolate, dicofol, amitraz, BPPS, benzomate, hexathiazox, fenbutatin oxide, polynactin, chinomethionat, CPCBS, tetradifon, avermectin, milbemectin, clofentezine, cyhexatin, pyridaben, fenpyroxymate, tebufenpyrad, pyrimidifen, fenothiocarb, dienochlor, and the like.

Plant growth regulators: gibberellins (for example, gibberellin A3, gibberellin A4, gibberellin A7), IAA, NAA, and the like.

Herbicides:

Anilide herbicides; diflufenican, propanil, and the like.

Chloroacetianilide herbicides; alachlor, pretilachlor, and the like.

Aryloxyalkanoic acid herbicides; 2,4-D, 2,4-DB, and the like.

Aryloxyphenoxyalkanoic acid herbicides; diclofop-methyl, fenoxaprop-ethyl, and the like.

Arylcarboxylic acid herbicides; dicamba, pyrithiobac, and the like.

Imidazoline herbicides; imazaquin, imazethapyr, and the like.

Urea herbicides; diuron, isoproturon, and the like.

Carbamate herbicides; chlorpropham, phenmedipham, and the like.

Thiocarbamate herbicides; thiobencarb, EPTC, and the like.

Dinitroaniline herbicides; trifluralin, pendimethalin, and the like.

Diphenyl ether herbicides; acifluorfen, fomesafen, and the like.

Sulfonylurea herbicides; bensulfuron-methyl, nicosulfuron, and the like.

Triazinone herbicides; metribuzin, metamitron, and the like.

Triazine herbicides; atrazine, cyanazin, and the like.

Triazopyrimidine herbicides; flumetsulam, and the like.

Nitrile herbicides; bromoxinil, dichlobenil, and the like.

Phosphoric acid herbicides; glyphosate, glufosinate, and the like.

Quaternary ammonium salt herbicides; paraquat, difenzoquat, and the like.

Cyclic imide herbicides; flumiclorac-pentyl, fluthiacet-methyl, and the like.

Benzoylaminopropionic acid herbicides; benzoylprop-ethyl, furanprop-ethyl, and the like.

Other herbicides; isoxaben, ethofumesate, oxadiazon, piperophos, daimuron, bentazone, benfuresate, difenzoquat, naproanilide, triazophenamide, quinchlorac, clomazone, sulcotrione, cinmethylin, dithiopyr, pyrazolate, pyridate, and flupoxam, and cyclohexanedione herbicides such as sethoxydim, tralkoxydim, and the like.

Synergists/Antidotes; octachlorodipropyl ether, piperonyl butoxide, cyneprin, IBTA, benoxacor, cloquintocet-methyl, ciometranil, dichlormid, fenchlorazole-ethyl, fencloram, flurazole, flaxofenimi, furilazole, mefenpyr-diethyl, MG191, naphthalic anhydride, oxabetrinil, neonicotinoid-based compounds, and the like.

Antibacterial/antifungal/antialgae agents; trialkyltriamine, ethanol, isopropyl alcohol, propyl alcohol, trisnitro, chlorobutanol, pronopol, glutaraldehyde, formaldehyde, α-bromcinnamaldehyde, scane M-8, caisson CG, NS-500W, BIT, n-butyl BIT, allyl isothiocyanate, thiobendazole, methyl 2-benzimidazolyl carbamate, lauricidine, biovan, triclocarban, halocarban, glasisicar, benzoic acid, sorbic acid, caprylic acid, propionic acid, 10-undecylenic acid, potassium sorbate, potassium propionate, potassium benzoate, monomagnesium phthalate, zinc undecylenate, 8-hydroxyquinoline, copper quinoline, TMTD, triclosan, dichlohelanilide, tolyfluanid, milt protein, egg white lysozyme, benthiazole, sodium carbam, triazine, tebuconazole, hinokithiol, tetrachloroisophthalonitrile, tectamer 38, chlorhexidine gluconate, chlorhexidine hydrochloride, polyhexamethylene biguanide, polybiguanide hydrochloride, danthoprom, clidant, sodium pyrithion, zinc pyrithion, densil, kappa-pyrithion, thymol, isopropyl methyl phenol, OPP, phenol, butyl paraben, ethyl paraben, methyl parabenzen, propyl parabenzene, metacresol, orthocresol, paracresol, sodium orthophenyl phenol, chlorofen, parachlorophenol, parachloro methaxylate, parachlorocresol, fluorfolpet, polylysine, biopan P-1487, Jote methylparatolylsulfone, polyvinylpyrrolidone parachloroisocyanel, hydrogen peroxide, stabilized chlorine dioxide, peracetic acid, copper naphthenate, novalon AG 300, silver chloride, titanium oxide, silver, zinc-calcium phosphate, Silver Ace, silver-zinc aluminosilicate, silver-zinc zeolite, novalon AGZ330, phorone killer, dimmer 136, benzalkonium chloride, didecyl dimethyl ammonium chloride, bardack 2250/80, benzotonium chloride, Hyamine 3500J, cetylammonium bromide, Cetrimide, CTAB, Cetavlon, Dimmer-38, benzalkonium chloride, Hyamine 3500J, BARDAC™ 170P, DC-5700, cetyl pyridinium chloride, chitosan, deuron, DCMU, prepentol A6, CMI, 2Cl-OIT, BCM, ZPT, BNP, OIT, IPBC, TCMSP, and the like.

Synthetic pyrethroid insecticides can be preferably exemplified because an insecticidal effect can be synergically exerted when mixed with the clathrate compound of the present invention. Specific examples of the synthetic pyrethroid insecticide include acrinathrin, allethrin, bioallethrin, barthrin, bifenthrin, bioethanomethrin, cyclethrin, cyclopro-thrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox (2-(4-ethoxyphenyl)-2-methylpropyl 3-phenoxybenzyl ether), flufenprox, halfenprox, protrifenbute, silafluofen, and the like.

2) Concentration Control Method

The concentration control method of the present invention is characterized by containing a step of maintaining the saturated solubility of the agricultural chemical active ingredient in water within a predetermined concentration range by including the agricultural chemical active ingredient having ready water-solubility in an interior space formed of a polymolecular host compound.

The polymolecular host compound is appropriately selected and the agricultural chemical active ingredient is included in an interior space formed of the polymolecular host compound, thereby maintaining the saturated solubility of the agricultural chemical active ingredient in water within a predetermined concentration range. When a clathrate compound including an agricultural chemical active ingredient is allowed to exist in water, the concentration of the agricultural chemical active ingredient in water does not reach the saturated concentration of the ingredient and can be controlled to a predetermined value that is lower than the saturated concentration. The predetermined value is decided by various factors, but is preferably controlled by the kind of host compound to be used.

The polymolecular host compound and agricultural chemical active ingredient having ready water-solubility to be used are not specifically limited and examples thereof are the same as those described for the clathrate compound.

3) Agricultural Chemical Formulation

The agricultural chemical formulation of the present invention preferably contains the clathrate compound of the present invention.

The agricultural chemical formulation of the present invention is preferably a seed treatment agent.

The form of the agricultural chemical formulation of the present invention is not specifically limited and examples thereof include wettable powders, wettable granules, water-soluble chemicals, granular water-soluble chemicals, water-soluble liquid formulations, granules, powders, emulsifiable concentrates, water-soluble chemicals, emulsions, suspoemulsions, microcapsules, and sol formulations (also referred to as SC (Suspension Concentrate) agents or flowables). Among these, sol formulations are preferable because the clathrate compound of the present invention can be maintained in a stable state.

The sol formulation is a formulation obtained by dispersing in water a solid agricultural chemical active ingredient that is insoluble in water. In the present invention, the agricultural sol formulation can be obtained by dispersing in water the clathrate compound of the present invention with a surfactant, a thickener, and, if necessary, other auxiliaries such as an antifreezing agent.

The content ratio of the clathrate compound is usually from 10 to 60% by weight, and preferably from 25 to 45% by weight, based on the total weight of the agricultural chemical formulation.

The surfactant is an agent for dispersing the agricultural chemical active ingredient, uniformly and stably, for a long period.

The surfactant to be used is not specifically limited, and is preferably a nonionic surfactant or an anionic surfactant.

Examples of the nonionic surfactant include polyoxyethylene alkyl ether such as polyoxyethylene lauryl ether, polyoxyethylene alkyl phenyl ether, polyoxyethylene styryl phenyl ether, polyoxyethylene oleyl ether, polyoxyethylene octyl phenyl ether, sorbitan alkyl ester, polyoxyethylene sorbitan alkyl ester, and mixtures of at least two kinds thereof.

The HLB (hydrophilic-lipophilic balance) value of the nonionic surfactant is preferably 10 or less, and more preferably 7 or less.

The content ratio of the nonionic surfactant is preferably from 0.1 to 20% by weight, and more preferably from 0.1 to 10% by weight, based on the total weight of the agricultural chemical formulation.

Examples of the anionic surfactant include alkyl sulfate (Na salt, $NH_4$ salt, alkanolamine salt), dialkyl sulfosuccinate (Na salt, Ca salt, Mg salt), alkyl naphthalenesulfonate, alkylbenzenesulfonate, lignosulfonate, formaldehyde condensate of alkyl naphthalene sulfonate, polyoxyethylene alkyl ether phosphate (Na salt, alkanolamine salt), polycarboxylate, and mixtures of at least two kinds thereof.

The content ratio of the anionic surfactant is preferably from 0.1 to 20% by weight, and more preferably from 0.1 to 10% by weight, based on the total weight of the agricultural chemical formulation.

The thickener is an agent for preventing sedimentation of dispersed particles.

Examples of the thickener include organic water-soluble polymers such as xanthan gum, guar gum, carboxymethyl cellulose, polyvinyl pyrrolidone, carboxyvinyl polymer, acrylic polymer, starch derivative, and polysaccharides; and fine powdered solid carriers such as high-purity bentonite and white carbon.

The content ratio of the thickener is preferably from 0.01 to 10% by weight, and more preferably from 0.1 to 3% by weight, based on the total weight of the agricultural chemical formulation.

Examples of the other auxiliaries include antifreezing agents, antifoamers, and antiseptics. The content ratio of the other auxiliaries is usually from 0 to 15% by weight, and preferably from 0.1 to 8% by weight, based on the total weight of the agricultural chemical formulation. The addition of the other auxiliaries does not adversely affect the saturated solubility of the agricultural chemical active ingredient in water.

The method for preparing a sol formulation is not specifically limited and examples thereof include a method of dispersing the clathrate compound, a surfactant, a thickener and, if necessary, other auxiliaries in water using a high-speed mixer, and finely pulverizing the obtained slurry through mechanical pulverizing.

The pulverizing method is not specifically limited, and is preferably a wet pulverizing method using a colloid mill, a dyno mill, a ball mill or a sand grinder.

The average particle size of particles in the obtained sol formulation is usually from 0.7 to 2.5 µm, and is preferably from 1 to 2 µm because of high stability of the sol.

The sol formulation is likely to form large particles as a result of the growth of particles due to a change in temperature during storage (particle growth), or to form a mass as a result of aggregation of particles (caking). The sol formulation of the present invention has high dispersion stability because the clathrate compound of the present invention is used. Since saturated solubility of the agricultural chemical active ingredient having ready water-solubility is maintained at a low level, neither particle growth nor caking may occur even when stored for a long period.

The agricultural chemical formulation of the present invention exhibits an excellent residual ratio of the agricultural chemical active ingredient in the agricultural chemical formulation even when stored for a long period, because the agricultural chemical active ingredient is contained as the clathrate compound in the formulation.

According to the agricultural chemical formulation of the present invention, the saturated solubility of the agricultural chemical active ingredient having ready water-solubility can be set within a predetermined concentration range by appropriately selecting the polymolecular host compound to be used.

According to the agricultural chemical formulation of the present invention, since the saturated solubility in water of the agricultural chemical active ingredient having ready water-solubility can be maintained and controlled at a low level, it is made possible to prevent the agricultural chemical active ingredient from dissolving in water within a short period, and thus dissociating from the formulation. That is, elution of the agricultural chemical active ingredient into water can be controlled and active efficacy as an agricultural chemical can be exhibited for a long period.

The agricultural chemical formulation of the present invention can be used in the same manner as in the case of an application method of a conventionally known agricultural chemical formulation. For example, there can be exemplified a method of immersing seeds of field crops in a solution prepared by diluting a predetermined amount of the agricultural chemical formulation of the present invention in water for a predetermined time, followed by seeding, more specifically, a method of finely pulverizing the agricultural chemical formulation of the present invention to 100 µm or less, dispersing or dissolving the pulverized agricultural chemical formulation in a solvent, immersing seeds in the obtained solution, and coating the surface of seeds with the agricultural chemical formulation, or a method of seeding seed of field crops, and uniformly spraying a predetermined amount of a solution prepared by diluting the agricultural chemical formulation of the present invention with water.

The agricultural chemical formulation of the present invention contains the clathrate compound of the present invention and is therefore stable in the soil and also exhibits excellent residual effects.

The agricultural chemical formulation of the present invention can be used for various purposes other than agricultural purposes, for example, soil pest control agents, termite control agents, agents for clothes, pest insect control agents, wood pest insect control agents, bait agents, animal ectoparasite control agents, sanitary pest insect control agents, domestic communicable disease control agents, ship bottom paints, antialgal agents for fishing nets, antifungal agents for wood, biocides, and the like.

4) Agricultural Active Composition

The agricultural active composition of the present invention contains the clathrate compound of the present invention and the synthetic pyrethroid insecticide. The synthetic pyrethroid insecticide can exhibit a synergistically enhanced insecticidal effect when mixed with the clathrate compound of the present invention.

The content ratio of the synthetic pyrethroid is not specifically limited, but is usually from 0.05 to 20 parts by weight, preferably from 0.1 to 10 parts by weight, and more preferably from 0.2 to 5 parts by weight, based on 1 part by weight of the agricultural chemical active ingredient having ready water-solubility in the clathrate compound of the present invention.

The method of mixing the clathrate compound of the present invention with the synthetic pyrethroid is not specifically limited, and a method of mixing the clathrate compound of the present invention with the synthetic pyrethroid to prepare a formulation, a method of mixing an agricultural chemical formulation containing the clathrate compound of the present invention with the synthetic pyrethroid to prepare a formulation, a method of mixing the clathrate compound of the present invention with the synthetic pyrethroid and using the obtained mixture (tank-mix), and a method of (successively) treating almost simultaneously with the application time can all be employed.

EXAMPLES

The present invention will now be described in more detail by examples. However, the present invention is not limited to the following examples.

The melting point was measured using a melting point measuring apparatus (DSC220, manufactured by Seiko Instruments Inc.).

Example 1

24.4 g (110 mmol) of acetamiprid (melting point: 96.4° C.) and 19.9 g (50 mmol) of 1,1,2,2-tetrakis(4-hydroxyphenyl)ethane (TEP) were dissolved in 500 ml of ethyl acetate while stirring under reflux conditions. After the completion of dissolution, the solution was stirred for 30 minutes and allowed to stand at room temperature overnight. The precipitated crystals were collected by filtration to obtain Clathrate compound 1.

The inclusion ratio of the Clathrate compound 1 was as follows: TEP:acetamiprid=1:2, and the melting point was 162.7° C.

$^1$H-NMR spectrum (CDCl$_3$, internal standard: TMS) of the Clathrate compound 1 is shown in FIG. 1. In FIG. 1, the ordinate indicates the peak intensity and the abscissa indicates the chemical shift (ppm) value (the same as in FIG. 4, FIG. 7 and FIG. 10).

Figure 2:
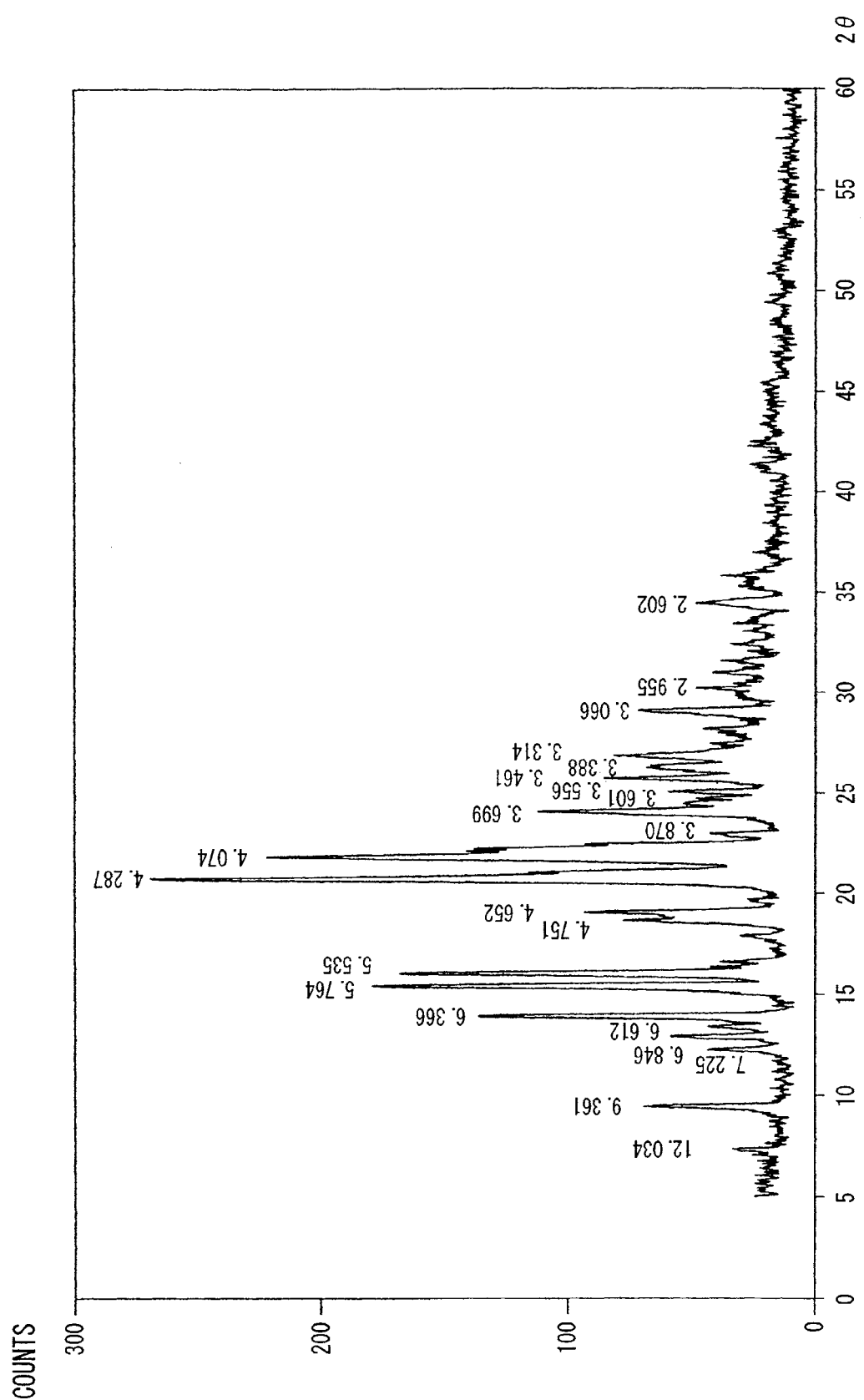
FIG. 2 is a graph showing the measurement results of XRD of Clathrate compound 1.

The measurement results of XRD of the Clathrate compound 1 are shown in FIG. 2. The ordinate indicates the intensity and the abscissa indicates the diffraction angle (the same as in FIG. 5, FIG. 8 and FIG. 12).

Figure 3:
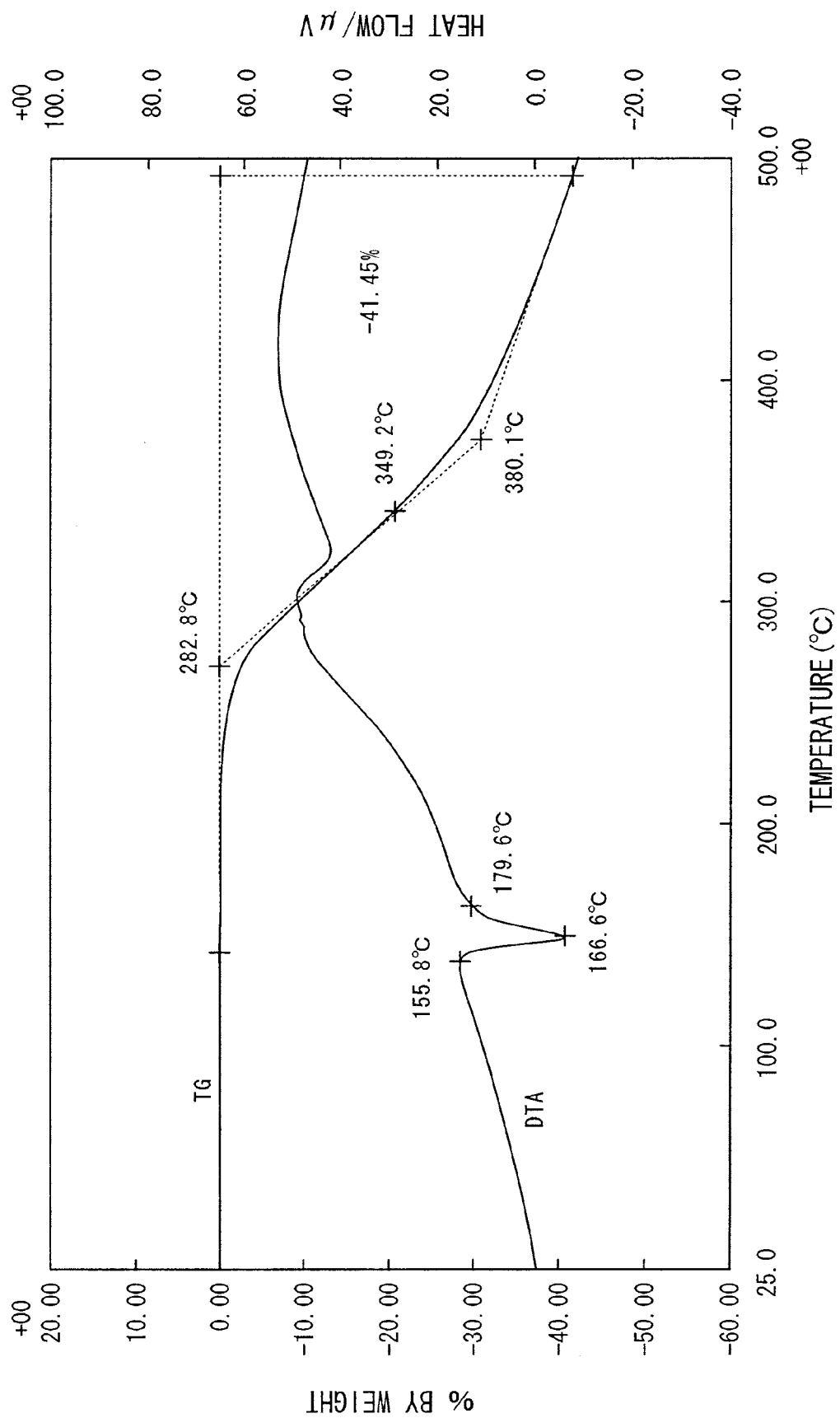
FIG. 3 is a graph showing the measurement results of TG-DTA of Clathrate compound 1.

The measurement results of TG-DTA of the Clathrate compound 1 are shown in FIG. 3. In FIG. 3, the ordinate (left) indicates the change in weight (% by weight), the ordinate (right) indicates Heat Flow/μV, and the abscissa indicates the temperature (° C.) (the same as in FIG. 6, FIG. 9 and FIG. 13).

Example 2

33.0 g (150 mmol) of acetamiprid (melting point: 96.4° C.) and 39.8 g (100 mmol) of 1,1,2,2-tetrakis(4-hydroxyphenyl)ethane (TEP) were dissolved in 220 ml of methanol while heating under reflux conditions. After the completion of dissolution, the solution was stirred for 30 minutes and allowed to stand at room temperature overnight. The precipitated crystals were collected by filtration to obtain Clathrate compound 2.

The inclusion ratio of the Clathrate compound 2 was as follows: TEP:acetamiprid:methanol=1:1:1, and the melting point was 167.5° C.

Figure 4:
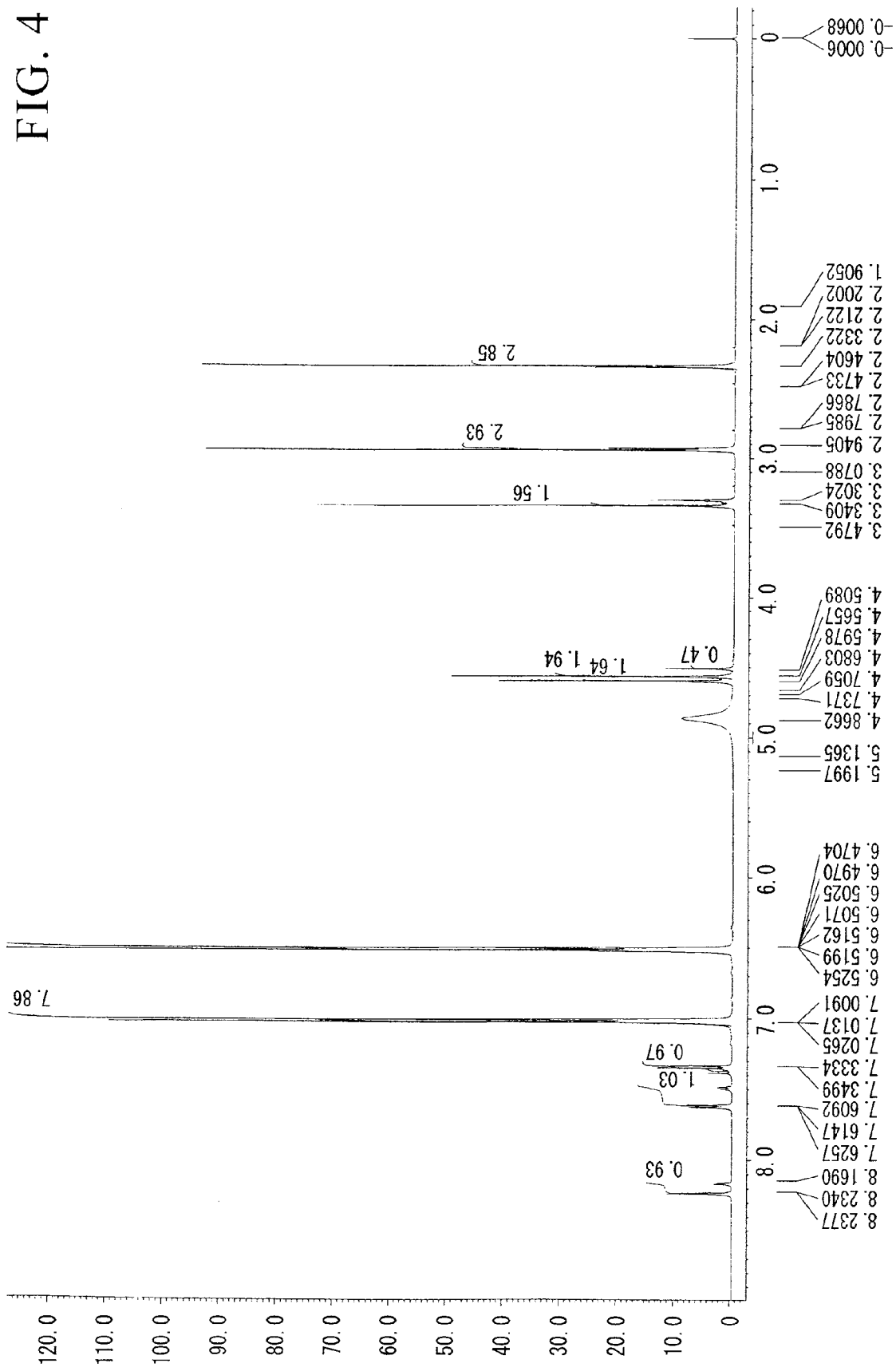
FIG. 4 is a graph showing a $^1$H-NMR spectrum of Clathrate compound 2.
Figure 5:
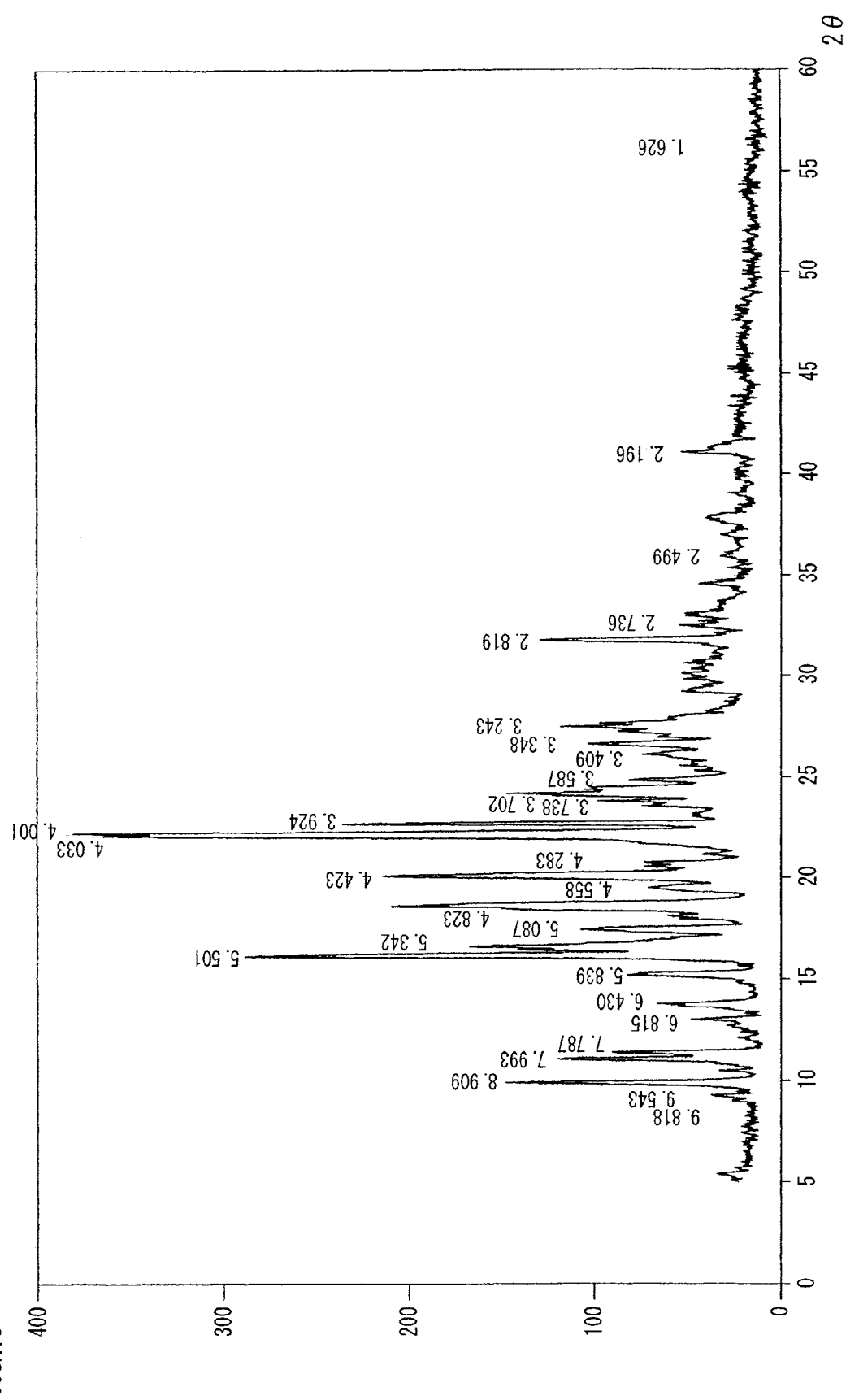
FIG. 5 is a graph showing the measurement results of XRD of Clathrate compound 2.
Figure 6:
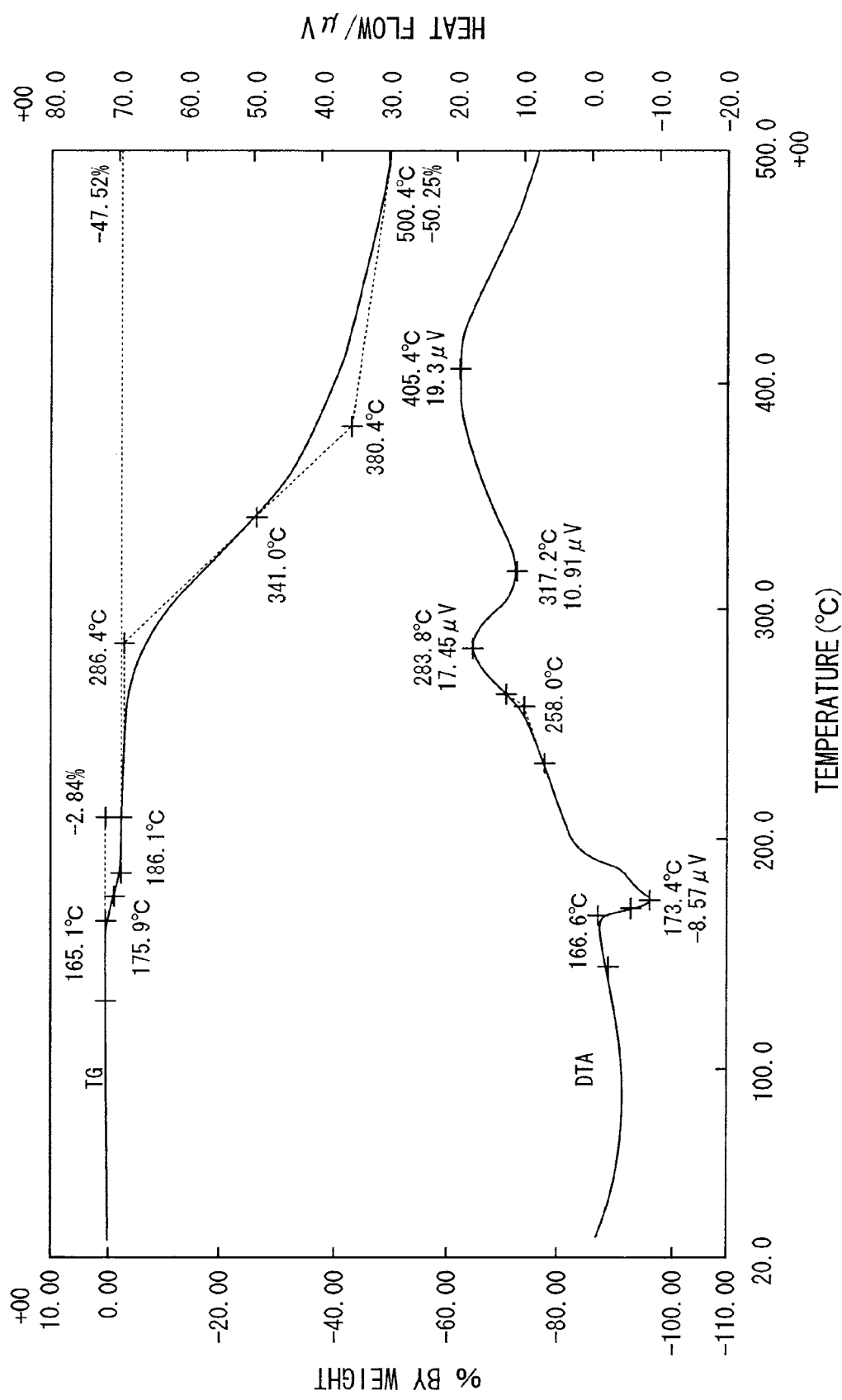
FIG. 6 is a graph showing the measurement results of TG-DTA of Clathrate compound 2.

$^1$H-NMR spectrum (CDCl$_3$, internal standard: TMS) of the Clathrate compound 2 is shown in FIG. 4, the measurement results of XRD are shown in FIG. 5, and the measurement results of TG-DTA are shown in FIG. 6.

Example 3

33.0 g (150 mmol) of acetamiprid (melting point: 96.4° C.) and 39.8 g (100 mmol) of 1,1,2,2-tetrakis(4-hydroxyphenyl)ethane (TEP) were dissolved in 220 ml of ethanol while heating under reflux conditions. After the completion of dissolution, the solution was stirred for 30 minutes and allowed to stand at room temperature overnight. The precipitated crystals were collected by filtration to obtain Clathrate compound 3.

The inclusion ratio of the Clathrate compound 3 was as follows: TEP:acetamiprid:ethanol=1:1:1, and the melting point was 167.5° C.

Figure 7:
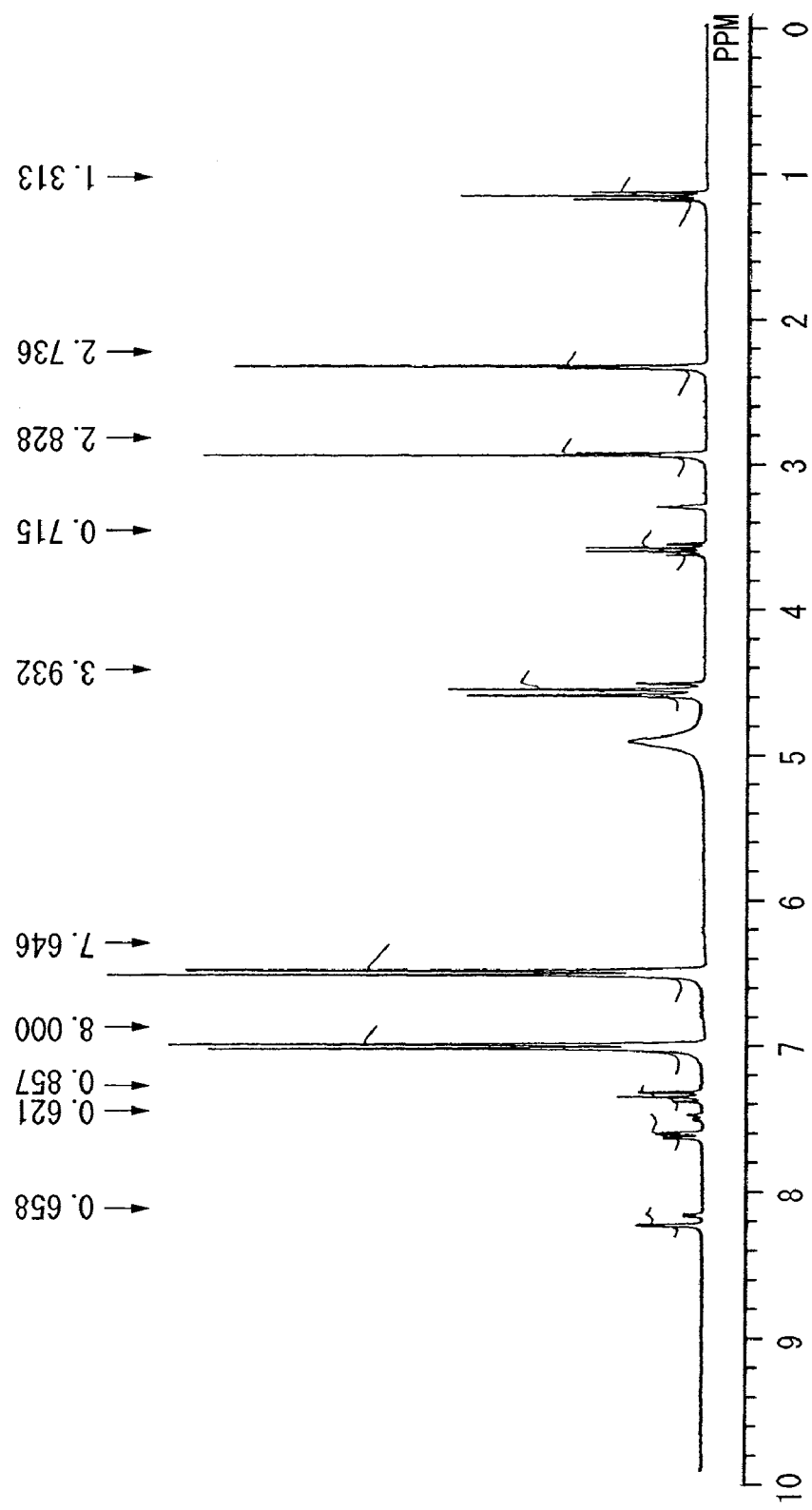
FIG. 7 is a graph showing a $^1$H-NMR spectrum of Clathrate compound 3.
Figure 8:
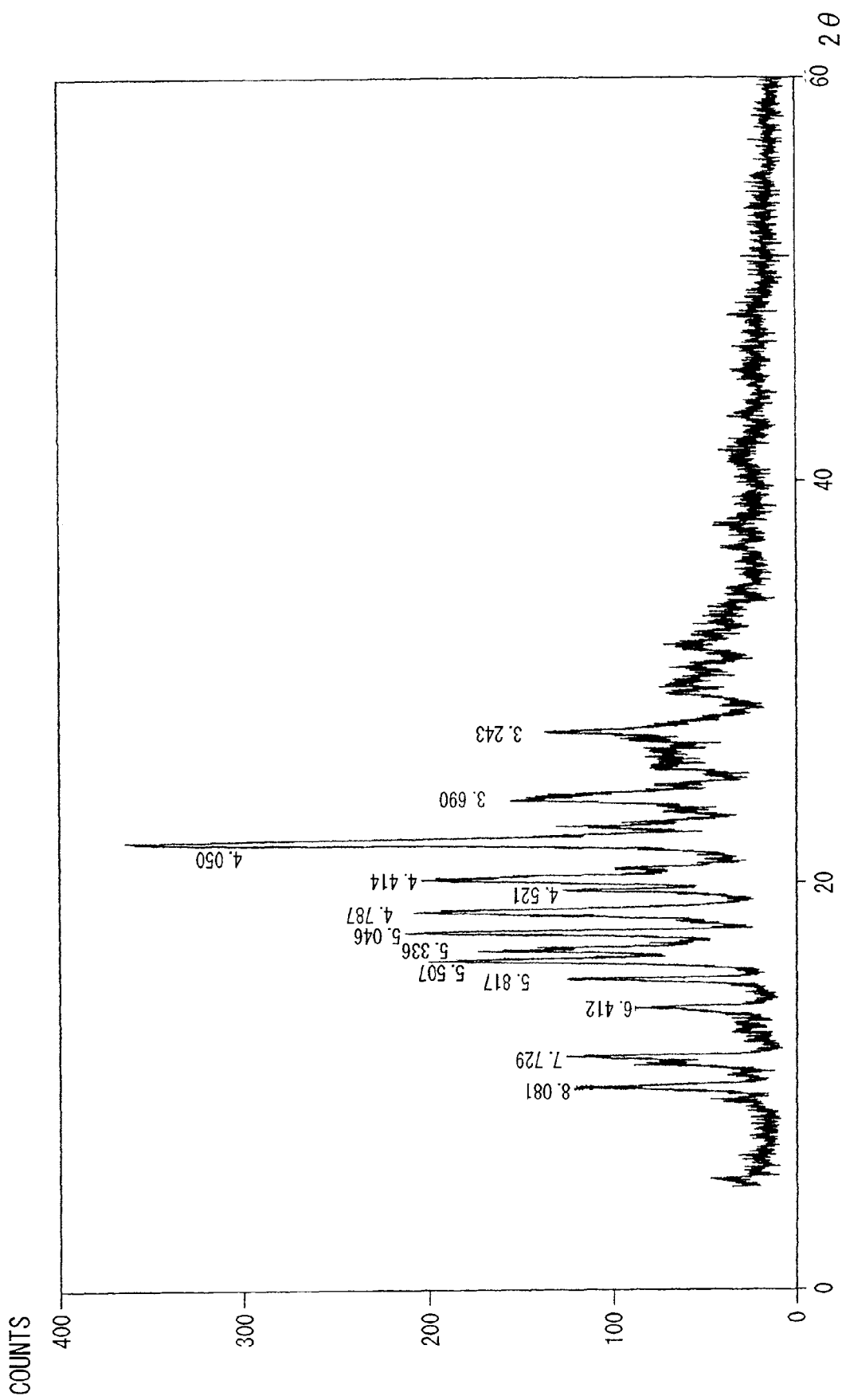
FIG. 8 is a graph showing the measurement results of XRD of Clathrate compound 3.
Figure 9:
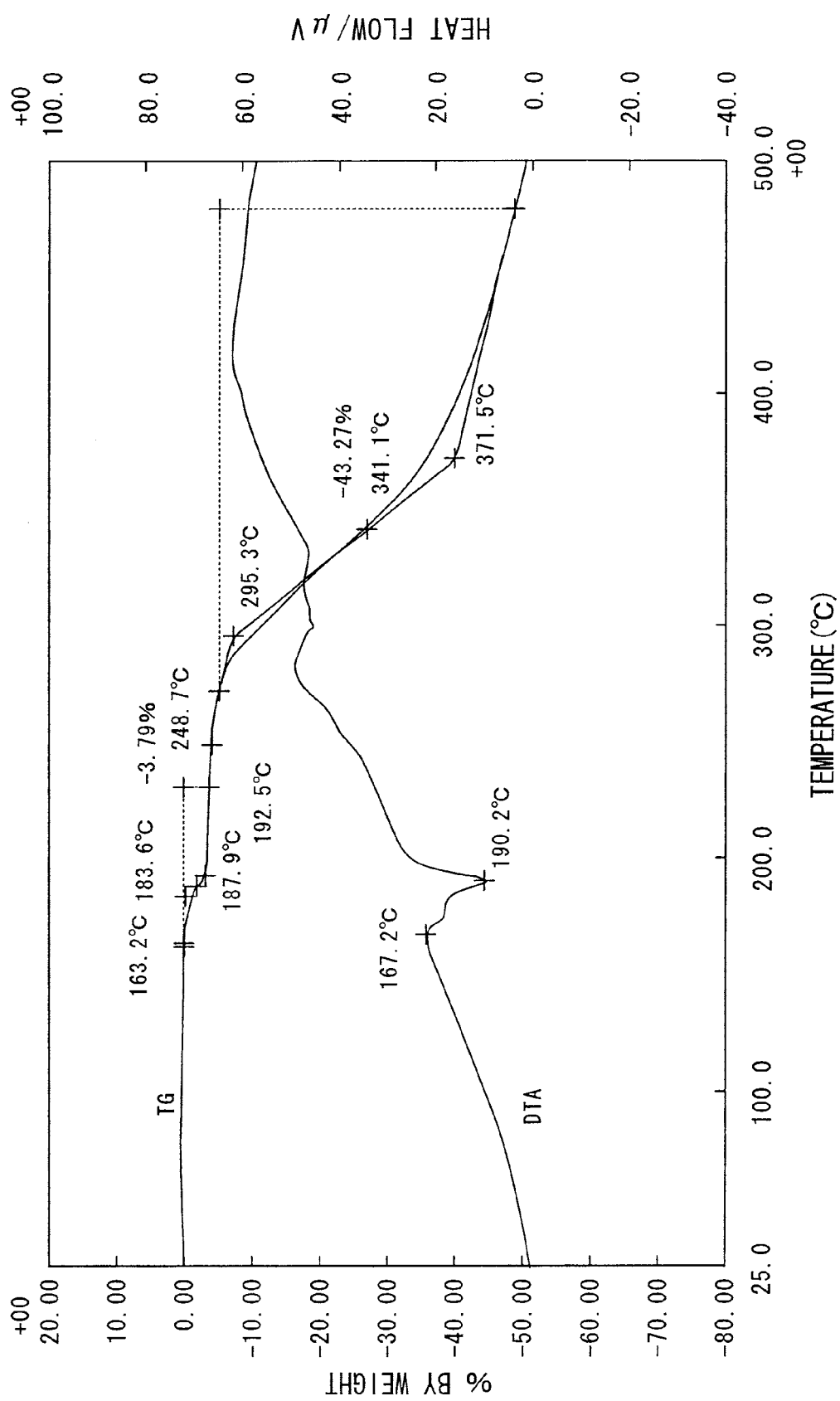
FIG. 9 is a graph showing the measurement results of TG-DTA of Clathrate compound 3.

$^1$H-NMR spectrum (CDCl$_3$, internal standard: TMS) of the Clathrate compound 3 is shown in FIG. 7, the measurement results of XRD are shown in FIG. 8, and the measurement results of TG-DTA are shown in FIG. 9.

Example 4

870 mg of acetamiprid (melting point: 96.4° C.), 1.26 g of 2,2',4,4'-tetrahydroxybenzophenone (THB) and 5.7 ml of ethanol were mixed and dissolved while stirring and heating under reflux conditions for 30 minutes. The solution was allowed to stand for 168 hours and the precipitated crystals were collected by filtration to obtain Clathrate compound 4.

Figure 10:
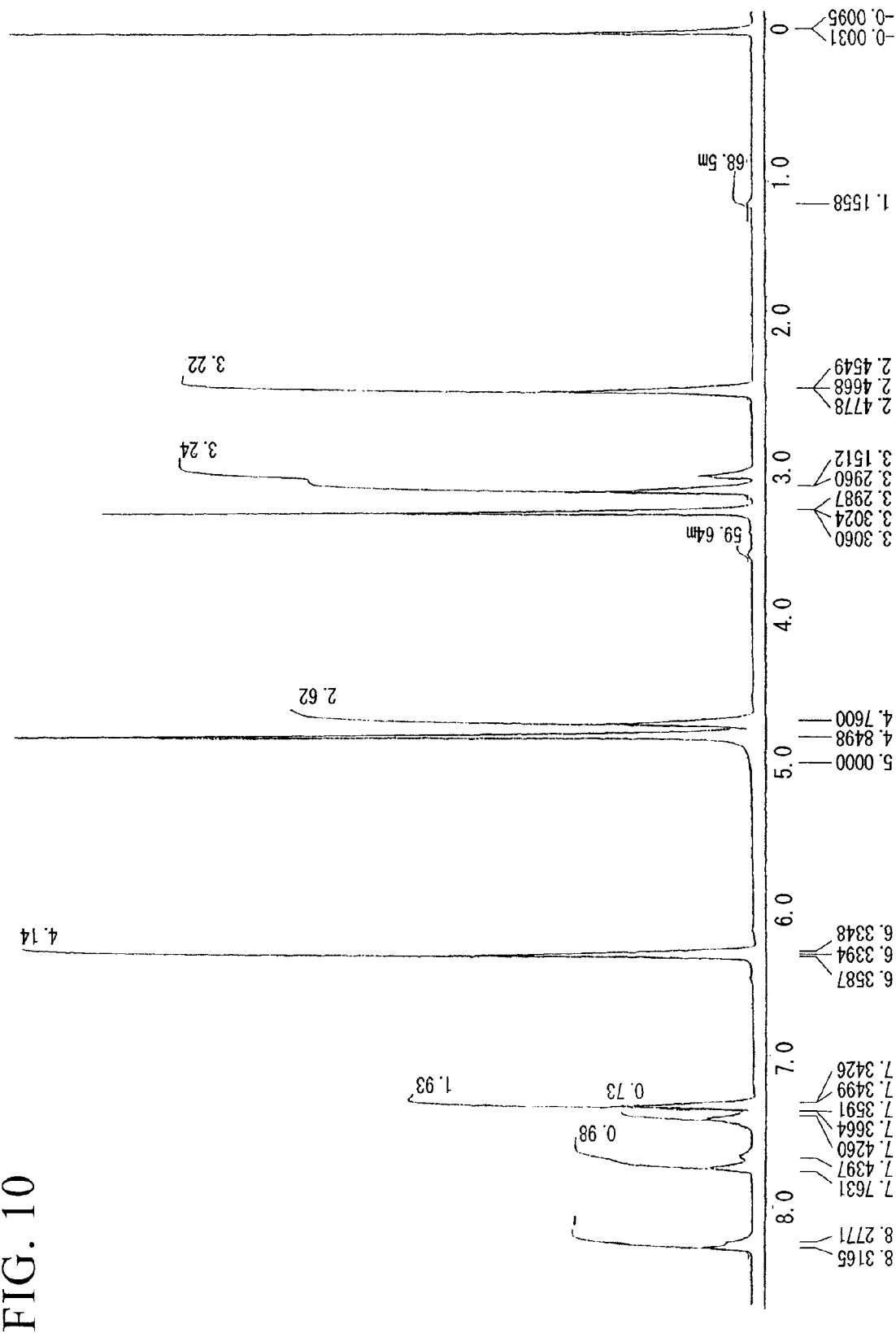
FIG. 10 is a graph showing a $^1$H-NMR spectrum of Clathrate compound 4.
Figure 11:
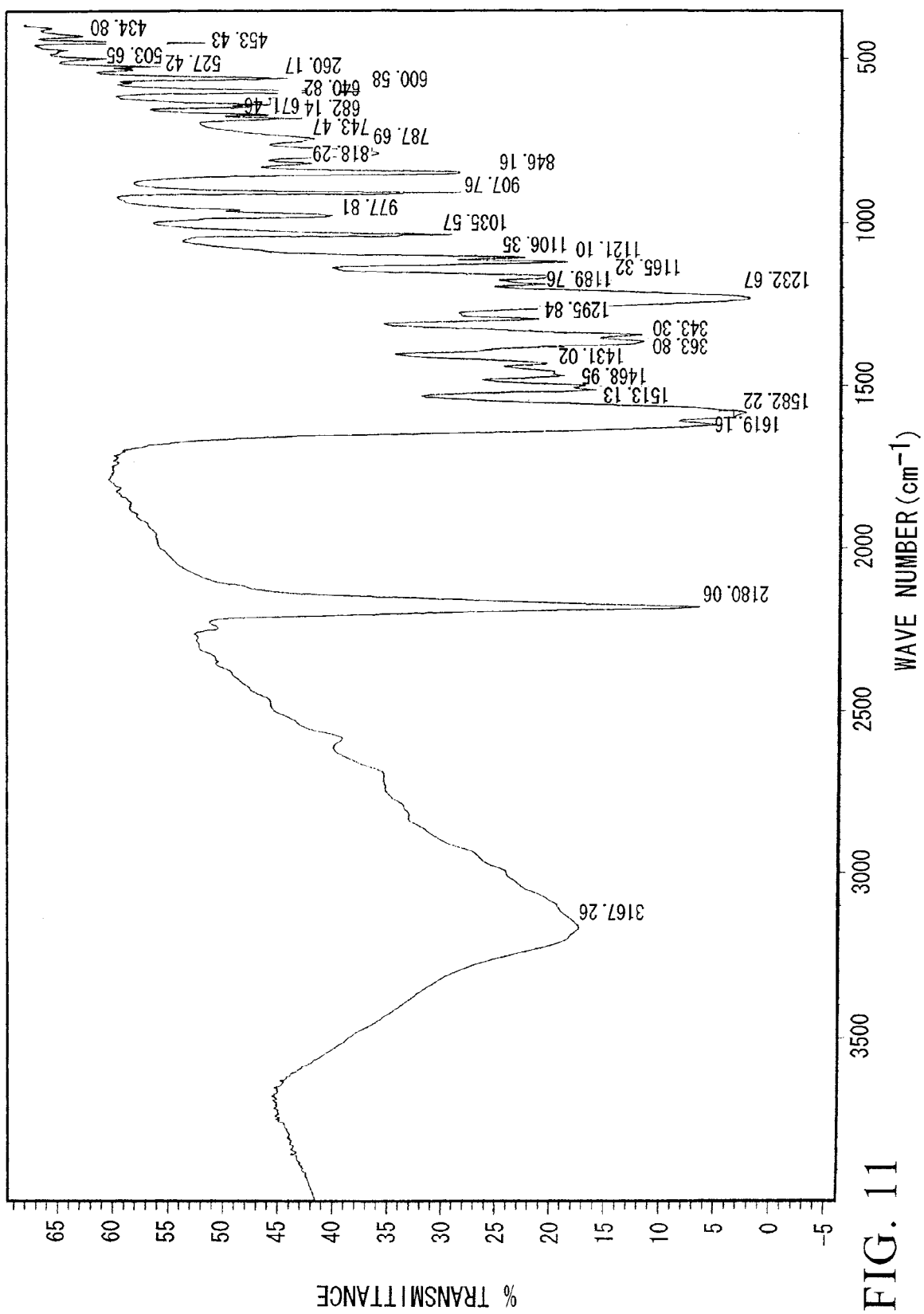
FIG. 11 is a graph showing an IR spectrum of Clathrate compound 4.
Figure 12:
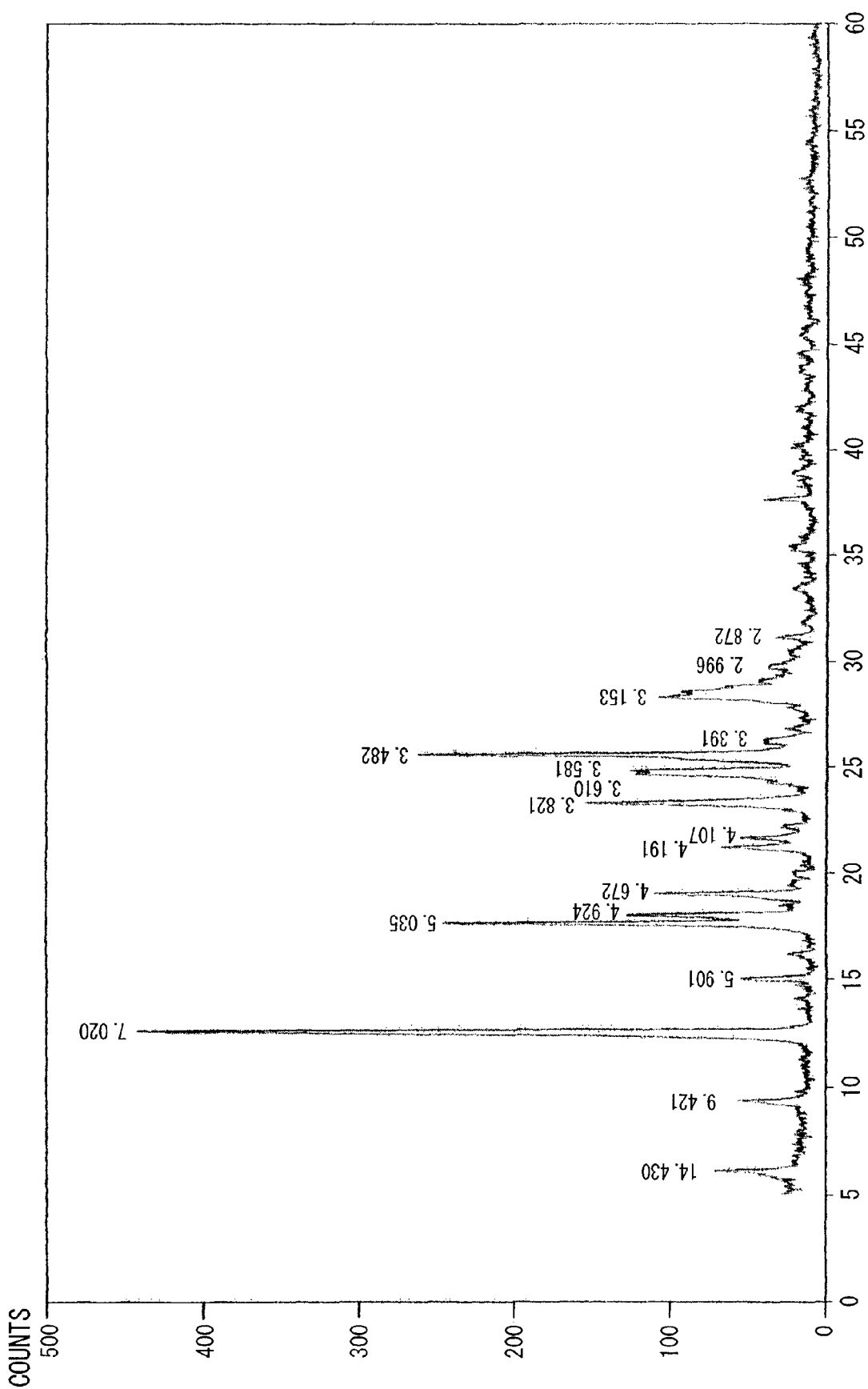
FIG. 12 is a graph showing the measurement results of XRD of Clathrate compound 4.
Figure 13:
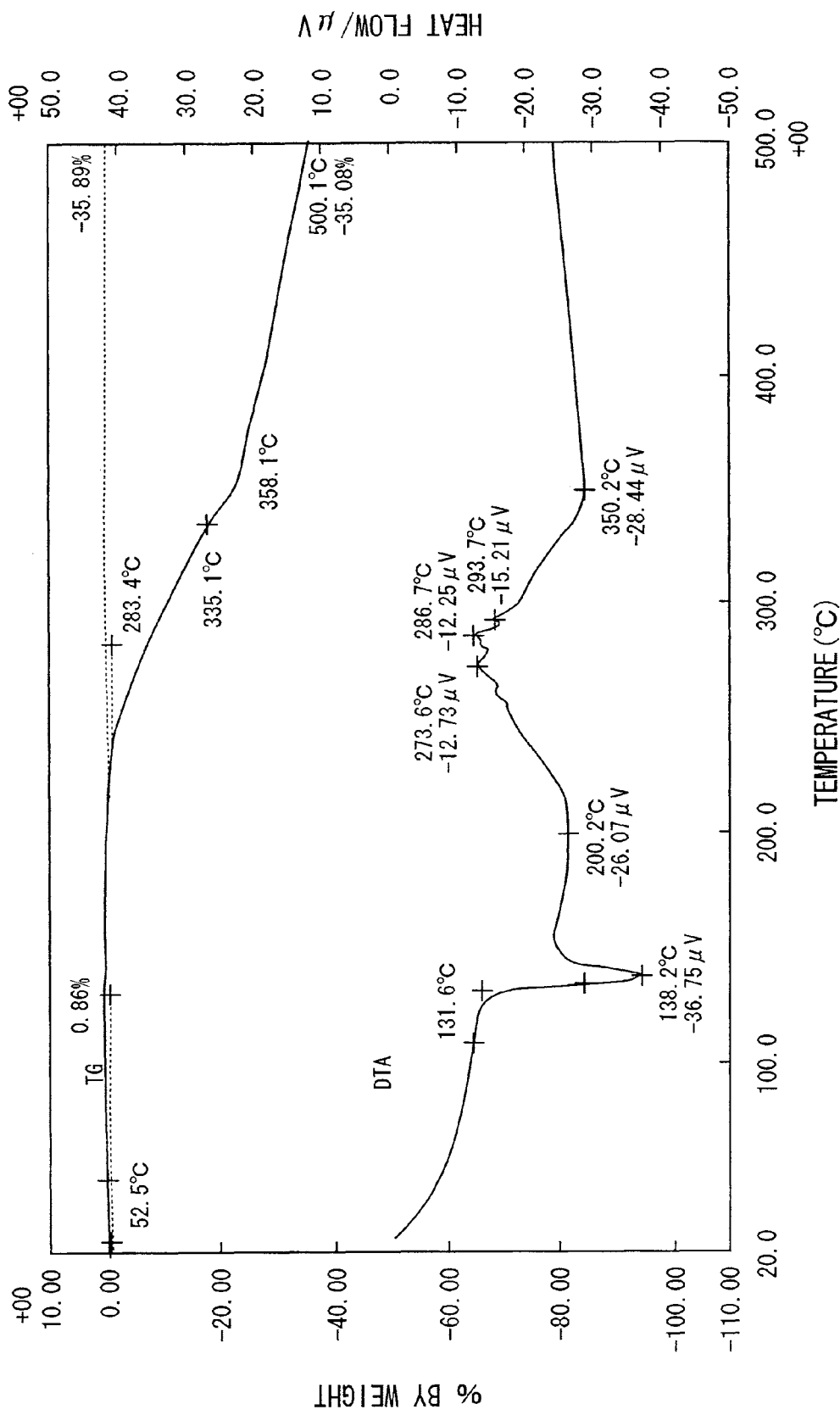
FIG. 13 is a graph showing the measurement results of TG-DTA of Clathrate compound 4.

$^1$H-NMR spectrum (CDCl$_3$, internal standard: TMS) of the Clathrate compound 4 is shown in FIG. 10, IR spectrum (KBr) is shown in FIG. 11, the measurement results of XRD are shown in FIG. 12, and the measurement results of TG- DTA are shown in FIG. 13. In FIG. 11, the ordinate indicates percentage transmittance and the abscissa indicates a wave number ($cm^{-1}$).

(Measurement of Saturated Solubility)

After weighing a fixed amount of each of the Clathrate compounds 1 to 4 obtained in Examples 1 to 4 and an acetamiprid as a control in a measuring flask, distilled water at 25° C. was added to obtain an equal volume. After stoppering and up-and-down shaking for 5 times, the measuring flask was allowed to stand in an incubator at 25° C. After up-and-down shaking for 5 times followed by sampling with the passage of time, water at 25° C. was added to obtain an equal volume again, and sampling was carried out up to 192 hours. The concentration of acetamiprid in the sampled solution was measured by HPLC and then the saturated solubility was calculated. The results are shown in Table 1.

As shown in Table 1, the saturated solubility after standing at 25° C. for 192 hours was as follows: Clathrate compound 1; 232 ppm, Clathrate compound 2; 238 ppm, Clathrate compound 3; 230 ppm, Clathrate compound 4; 373 ppm, acetamiprid; 3807 ppm.

tured by Takemoto Oil & Fat Co., Ltd.) and 1% by weight of Na alkyl naphthalenesulfonate (Newkalgen BX-C, manufactured by Takemoto Oil & Fat Co., Ltd.) as a surfactant were mixed and pulverized using a pin mill to obtain Wettable powder 1 to be contained in a formulation in an amount of 50% by weight.

Storage Stability Test 1 to 2 g of Sol formulation 1 was placed in an ampoule and stored in an incubator at 54° C. for 7 days (a), or alternately stored in incubators at 50° C. and –10° C. each for 3 days at 50° C., 3 days at –10° C., alternating for a total of 30 days (b). The content of acetamiprid was measured by high-performance liquid chromatography (HPLC) and the residual ratio of acetamiprid in the sol formulations was calculated. As a result, the residual ratio of acetamiprid in (a) and (b) was substantially 100%. This shows that the stability of acetamiprid contained therein can be maintained even if Sol formulation 1 is exposed to an environment where the temperature drastically changes for a long period. Sol formulation 1 in (a) had an average particle size of 1.6 µm and showed a lesser particle growth rate, and also caking did not occur.

TABLE 1

| | Concentration of acetamiprid (ppm) | | | | | |
|---|---|---|---|---|---|---|
| Compounds | 1 hour | 3 hours | 24 hours | 48 hours | 72 hours | 192 hours |
| Clathrate compound 1 | 121 ppm | 134 ppm | 193 ppm | 210 ppm | 221 ppm | 232 ppm |
| Clathrate compound 2 | 72 ppm | 79 ppm | 161 ppm | 200 ppm | 217 ppm | 238 ppm |
| Clathrate compound 3 | 156 ppm | 156 ppm | 163 ppm | 179 ppm | 200 ppm | 230 ppm |
| Clathrate compound 4 | 238 ppm | 244 ppm | 306 ppm | 333 ppm | 346 ppm | 373 ppm |
| Acetamiprid | 2,822 ppm | 3,273 ppm | 3,734 ppm | 3,776 ppm | 3,752 ppm | 3,807 ppm |

As is apparent from the results shown in Table 1, the saturated solubility of acetamiprid was drastically lowered in the Clathrate compounds 1 to 4. It was also found that the saturated solubility after a lapse of long period of time (after 192 hours) varied depending on the polymolecular host compound used and the saturated solubility showed substantially the same value (Clathrate compounds 1, 2 and 3) when using the same polymolecular host compound, even if the method for preparing the clathrate compound varied.

Example 5

35.0% by weight of Clathrate compound 1, 5.0% by weight of polyoxyethylene lauryl ether (Newcol 2303, manufactured by Nippon Nyukazai Co., Ltd.) as a surfactant, 2.5% by weight of Na dioctyl sulfosuccinate (Newkalgen EP-70G, manufactured by Takemoto Oil & Fat Co., Ltd.), 0.2% by weight of a thickener (Roadpole 23, manufactured by Rhodia Nicca, Ltd.) and other auxiliaries, that is, 5.0% by weight of an antifreezing agent (propylene glycol), 0.5% by weight of an antifoamer (Antifoam SE39, manufactured by Wacker Asahikasei Silicone Co., Ltd.) and 0.1% by weight of an antiseptic (PROXEL GXL, manufactured by Avecia KK) were mixed with 51.7% by weight of water using a high-speed mixer. The obtained slurry was pulverized using a bead mill to obtain Sol formulation 1.

Sol formulation 1 had an average particle size of 1.3 µm.

Example 6

98% by weight of Clathrate compound 1, and 1% by weight of Na lignosulfonate (Newkalgen RX-B, manufac- Also 1 to 2 g of Wettable powder 1 was placed in a vinyl bag and the vinyl bag was placed in an aluminum laminate, and then the storage stability test (a) was carried out. As a result, the residual ratio of acetamiprid was substantially 100%, similarly to Sol formulation 1. After the test, the state of the powder was excellent and caking also did not occur.

Stability in Soil Test

The obtained wettable powder 1 was uniformly mixed with soil so as to control the content of acetamiprid to 1 mg based on 10 g of the soil. After storing in an incubator under the conditions of a temperature of 25° C. and a relative humidity of 90%, sampling was carried out every predetermined period. Acetamiprid in the soil was extracted with a solvent and analyzed by HPLC, and thus the residual ratio of acetamiprid was calculated.

The same test was carried out using a wettable powder containing 70% by weight of acetamiprid and the stability in soil (residual ratio) was measured. The results are shown in Table 2. In Table 2, half-life in the soil means the period (days) required to reduce the amount of acetamiprid added under these test conditions to half.

TABLE 2

| Lapsed days | Wettable powder 1 | Wettable powder containing 70% by weight of acetamiprid |
|---|---|---|
| 0 day | 100% | 100% |
| 7 days | 46% | 47% |
| 13 days | 45% | 35% |

TABLE 2-continued

| Lapsed days | Wettable powder 1 | Wettable powder containing 70% by weight of acetamiprid |
|---|---|---|
| 21 days | 27% | 23% |
| 28 days | 28% | 20% |
| Half-life in soil | 12.6 days | 10.5 days |

As is apparent from the results in Table 2, the half-life in soil of acetamiprid in Wettable powder 1 was longer than that of acetamiprid in the wettable powder containing 70% by weight of acetamiprid, and Wettable powder 1 had high stability in soil.

Test as Seed Treatment Agent

In to 3 ml of a solution (sticker solution) prepared by dissolving 5% by weight of polyvinyl alcohol (Gohsenol GL-05S, manufactured by Nippon Synthetic Chemical Industry Co., Ltd.) and 1% by weight of Na lignosulfonate (Newkalgen RX-B, manufactured by Takemoto Oil & Fat Co., Ltd.) as a surfactant in 94% by weight of water, Wettable powder 1 of Example 6 was dispersed so as to contain 70 mg of acetamiprid, and then 0.3 ml of this dispersion was placed in a vinyl bag with a zipper containing 20 g of wheat seeds (Norin No. 61). Immediately after that, the vinyl bag was closed, and the seeds were coated with the chemical by vigorously shaking for 30 seconds. These seeds were spread over a tray and then air-dried at room temperature overnight to obtain wheat seeds coated with 35 g of acetamiprid per 100 kg of seeds. The seeds were then planted in a No. 2 unglazed flower pot containing Kuroboku soil, followed by inoculation with adults and larvae of 20 wheat aphids per plant 40 days (or 50 days) later. The number of parasites was counted 2, 4, and 7 days after inoculation to evaluate the residual efficacy. In the case of treatment with a wettable powder containing 70% by weight of acetamiprid and no treatment as control, the same test was carried out. The results are shown in Table 3.

TABLE 3

| Formulations | Inoculated 40 days after seeding | | | Inoculated 50 days after seeding | | |
|---|---|---|---|---|---|---|
| | after 2 days | after 4 days | after 7 days | after 2 days | after 4 days | after 7 days |
| Wettable powder 1 | 2 | 0 | 0 | 19 | 29 | 32 |
| Wettable powder containing 70% by weight of acetamiprid | 7 | 7 | 38 | 40 | 43 | 76 |
| No treatment | 49 | 87 | 276 | 43 | 90 | 159 |

As is apparent from the results shown in Table 3, Wettable powder 1 exhibited high persistence of potency of an agricultural chemical active ingredient, compared with the wettable powder containing 70% by weight of acetamiprid.

Test as a Seed Treatment Agent Used in Combination with a Synthetic Pyrethroid Agent In 3.2 ml of a solution (sticker solution) prepared by dissolving 5% by weight of polyvinyl alcohol (Gohsenol GL-05S, manufactured by Nippon Synthetic Chemical Industry Co., Ltd.) and 1% by weight of Na lignosulfonate (Newkalgen RX-B, manufactured by Takemoto Oil & Fat Co., Ltd.) as a surfactant in 94% by weight of water, Wettable powder 1 of Example 6 was dispersed so as to contain 800 mg of acetamiprid, and then 0.24 g of this dispersion was placed in a vinyl bag with a zipper containing 8 g of rapeseeds. Immediately after that, the vinyl bag was closed, and the rapeseeds were coated with the chemical by vigorously shaking for 30 seconds. These seeds were spread over a tray and then air-dried at room temperature overnight to obtain rapeseeds coated with 500 g of acetamiprid per 100 kg of seeds.

In 1.1 g of bifenthrin SC agent (active ingredient: 7.2% by weight), Wettable powder 1 of Example 6 was dispersed so as to contain 80 mg of acetamiprid, and then 0.64 g of this dispersion (containing 40 mg of bifenthrin and 40 mg of acetamiprid) was placed in a vinyl bag with a zipper containing 8 g of rapeseeds. Immediately after that, the vinyl bag was closed, and the rapeseeds were coated with the chemical by vigorously shaking for 30 seconds. These seeds were spread over a tray and then air-dried at room temperature overnight to obtain rapeseeds coated with 500 g of bifenthrin and 500 g of acetamiprid per 100 kg of seeds.

The obtained seeds were seeded in a No. 2 pot containing alluvial soil and then cultivated in a greenhouse. 15 days after seeding, rape seedlings were transferred to a cage in which 100 imagines of striped flea beetle were released. 2 days after standing, the number of incidences of insect damage due to imagines of striped flea beetle of 3 plants in each experimental plot was counted. In the case of a treatment with a wettable powder containing 70% by weight of acetamiprid or only a bifenthrin SC agent so as to coat seeds with 500 g of the active ingredient thereof per 100 kg of seeds, and no treatment as control, the same test was carried out. The results are shown in Table 4.

TABLE 4

| Formulations | Treatment amount g/100 kg of seeds | Number of incidences of insect damage/ 3 plants after 15 days | Insecticidal ratio % after 15 days |
|---|---|---|---|
| Wettable powder 1 + bifenthrin | 500 + 500 250 + 250 | 40 58 | 89.9 85.4 |
| Wettable powder 1 | 500 | 65 | 83.7 |
| Bifenthrin | 500 | 98 | 75.4 |
| Wettable powder containing 70% by weight of acetamiprid | 500 | 80 | 79.9 |
| No treatment | — | 398 | |

As is apparent from the results shown in Table 4, Wettable powder 1 exhibited a higher insecticidal effect against striped flea beetles compared with the wettable powder containing 70% by weight of acetamiprid. It was also found that the insecticidal effect against striped flea beetles was enhanced by using in combination with bifenthrin as a synthetic pyrethroid agent, compared with a treatment with only Wettable powder 1 or bifenthrin, and that a synergistic effect was recognized between Wettable powder 1 and the synthetic pyrethroid agent.

Test as an Agent Against Termites
[Potency Test as a Soil Treatment Agent Against Termites]

A chemical solution was prepared by dispersing 0.5 g of Wettable powder 1 obtained in Example 6 in 1.6 L of tap water. 1 ml of the obtained chemical solution was added to 14 g of kuroboku soil, followed by uniform mixing with stirring. The treated soil was placed in an incubator at 36° C. and water lost by evaporation was added every 7 days, so as to return to the initial weight, followed by mixing while stirring. 21 days after the treatment, the treated soil was filled in a vinyl chloride tube (inner diameter: 11 mm, length: 5 cm) and the tube was connected to the bridge portion in height of 2 cm from the bottom of two PET resin test vessels (inner diameter: 5 cm, height: 11 cm). In one test vessel, 30 g of a non-treated soil was placed. After 2 days, 60 worker ants and one soldier ant of the Reticulitermes speratus Kolbe species were inoculated. In the other test vessel, 5 g of cut corrugated cardboard as bait and 5 ml of tap water were placed. The test vessel was placed in an incubator at 25° C. and the active efficacy was evaluated by observing the state of boring of the treated soil, the state of behavior and the state of health for 21 days. A plot treated with a wettable powder containing 70% by weight of acetamiprid (the same amount of active ingredient) and a plot treated with no chemical were used as control. The test was repeated twice. The results are shown in Table 5.

TABLE 5

| Formulations | Repetition | Boring degree* | | | | | | |
|---|---|---|---|---|---|---|---|---|
| | | 1 DAT | 3 DAT | 5 DAT | 7 DAT | 10 DAT | 14 DAT | 21 DAT |
| Wettable powder | A | 1 | 1 | 1 | 1 | 1 | 1 | 1 |
| | B | 0 | 0 | 0 | 0 | 0 | 0 | 0 |
| | Average | 0.5 | 0.5 | 0.5 | 0.5 | 0.5 | 0.5 | 0.5 |
| Wettable powder containing 70% by weight of acetamiprid | A | 0 | 0 | 5 | 5 | 5 | 5 | 5 |
| | B | 1 | 1 | 2 | 2 | 3 | 5 | 5 |
| | Average | 0.5 | 0.5 | 3.5 | 3.5 | 4 | 5 | 5 |
| No treatment | A | 5 | 5 | 5 | 5 | 5 | 5 | 5 |
| | B | 5 | 5 | 5 | 5 | 5 | 5 | 5 |
| | Average | 5 | 5 | 5 | 5 | 5 | 5 | 5 |

*Boring degree 0: no boring to test soil was observed
Boring degree 1: boring distance of less than 1 cm
Boring degree 2: boring distance of less than 2 cm
Boring degree 3: boring distance of less than 3 cm
Boring degree 4: boring distance of less than 4 cm
Boring degree 5: boring distance of not less than 4 cm As is apparent from the results shown in Table 5, Wettable powder 1 exhibited enhanced insecticidal effects on the soil against Reticulitermes speratus Kolbe compared with the wettable powder containing 70% by weight of acetamiprid.

What is claimed is:

1. A clathrate compound, comprising:
a polymolecular host compound as a host compound; and
an agricultural chemical active ingredient having a saturated solubility in water at 25° C. of not less than 500 ppm as a guest compound;
wherein the polymolecular host compound is a tetrakisphenol compound represented by formula (I):

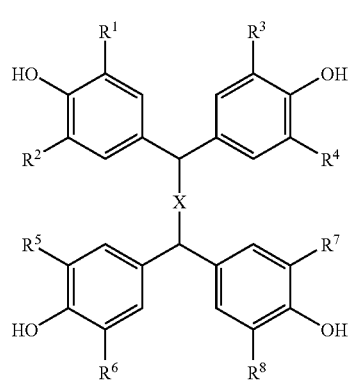

where:
X represents:
$(CH_2)_n$ where n represents an integer of 0 to 3, or
a phenylene group which may have a substituent; and
$R^1$ to $R^8$ each independently represents:
a hydrogen atom,
an alkyl group having 1 to 6 carbon atoms,
a phenyl group which may have a substituent,
a halogen atom, or
an alkoxyl group having 1 to 6 carbon atoms.

2. A clathrate compound, comprising:
a polymolecular host compound as a host compound; and
an agricultural chemical active ingredient having a saturated solubility in water at 25° C. of not less than 500 ppm as a guest compound;
wherein the polymolecular host compound is a hydroxybenzophenone compound represented by formula (II):

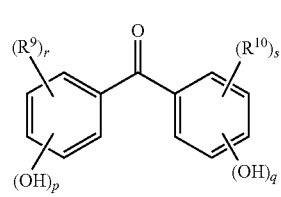

where:
$R^9$ and $R^{19}$ each independently represents:
an alkyl group having 1 to 6 carbon atoms,
a halogen atom, or
an alkoxyl group having 1 to 6 carbon atoms;
r and s each independently represents an integer of 0 to 4; and
p and q each independently represents an integer of 1 to 4.

3. The clathrate compound according to claim 1, wherein the agricultural chemical active ingredient is a neonicotinoid compound.

4. The clathrate compound according to claim 3, wherein the neonicotinoid compound is at least one selected from the group consisting of nitenpyram, imidacloprid, acetamiprid, thiamethoxam, clotianidin, thiacloprid, and dinotefuran.

5. The clathrate compound according to claim 2, wherein the agricultural chemical active ingredient is a neonicotinoid compound.

6. The clathrate compound according to claim 5, wherein the neonicotinoid compound is at least one selected from the group consisting of nitenpyram, imidacloprid, acetamiprid, thiamethoxam, clotianidin, thiacloprid, and dinotefuran.

* * * * *